(12) United States Patent
Park et al.

(10) Patent No.: US 9,855,218 B2
(45) Date of Patent: Jan. 2, 2018

(54) DEVICE FOR LARGE-SCALE MICROPARTICLE PRODUCTION AND METHOD OF USING THE SAME

(71) Applicant: AKINA, INC., West Lafayette, IN (US)

(72) Inventors: Kinam Park, West Lafayette, IN (US); Sarah Michelle Skidmore, Lafayette, IN (US); Larry Fultz, Lafayette, IN (US); Yeonhee Yun, West Lafayette, IN (US); Byung Kook Lee, West Lafayette, IN (US)

(73) Assignee: Akina, Inc., West Lafayette, IN (US)

( * ) Notice: Subject to any disclaimer, the term of this patent is extended or adjusted under 35 U.S.C. 154(b) by 193 days.

(21) Appl. No.: 14/896,276

(22) PCT Filed: Jun. 9, 2014

(86) PCT No.: PCT/US2014/041583
§ 371 (c)(1),
(2) Date: Dec. 4, 2015

(87) PCT Pub. No.: WO2014/197904
PCT Pub. Date: Dec. 11, 2014

(65) Prior Publication Data
US 2016/0128941 A1    May 12, 2016

Related U.S. Application Data

(60) Provisional application No. 61/832,297, filed on Jun. 7, 2013.

(51) Int. Cl.
*A61K 9/16* (2006.01)
*B05D 1/26* (2006.01)
*B05D 1/42* (2006.01)
*B29C 31/04* (2006.01)
*B29C 39/04* (2006.01)
*B29C 41/02* (2006.01)
*B02C 19/00* (2006.01)

(52) U.S. Cl.
CPC ............ *A61K 9/1682* (2013.01); *B02C 19/00* (2013.01)

(58) Field of Classification Search
None
See application file for complete search history.

(56) References Cited

U.S. PATENT DOCUMENTS

| | | | |
|---|---|---|---|
| 3,825,643 A * | 7/1974 | Hillier et al. | ........... B29C 67/08 264/161 |
| 4,060,031 A | 11/1977 | Philipp | |
| 5,040,342 A | 8/1991 | McGuire et al. | |
| 5,871,818 A | 2/1999 | Button et al. | |
| 8,986,596 B2 * | 3/2015 | Cheng | ................. B81C 1/00214 264/297.1 |
| 2002/0083857 A1 | 7/2002 | Bardet et al. | |
| 2006/0116059 A1 | 6/2006 | Chen et al. | |

(Continued)

OTHER PUBLICATIONS

International Search Report and Written Opinion, International Application No. PCT/US2014/041583, dated Sep. 16, 2014, 10 pages.

*Primary Examiner* — Mary Lynn F Theisen
(74) *Attorney, Agent, or Firm* — Barnes & Thornburg LLP

(57) ABSTRACT

A semi-automated device that provides a mechanism to produce large-scale microparticle formulations of specific sizes with no scum layer formation, and a method for using the device.

20 Claims, 12 Drawing Sheets

(56) References Cited

U.S. PATENT DOCUMENTS

2009/0136583 A1    5/2009  Park et al.
2009/0147655 A1    6/2009  Volk et al.
2011/0182805 A1*   7/2011  DeSimone ........... A61K 9/0097
                                              424/1.11

* cited by examiner

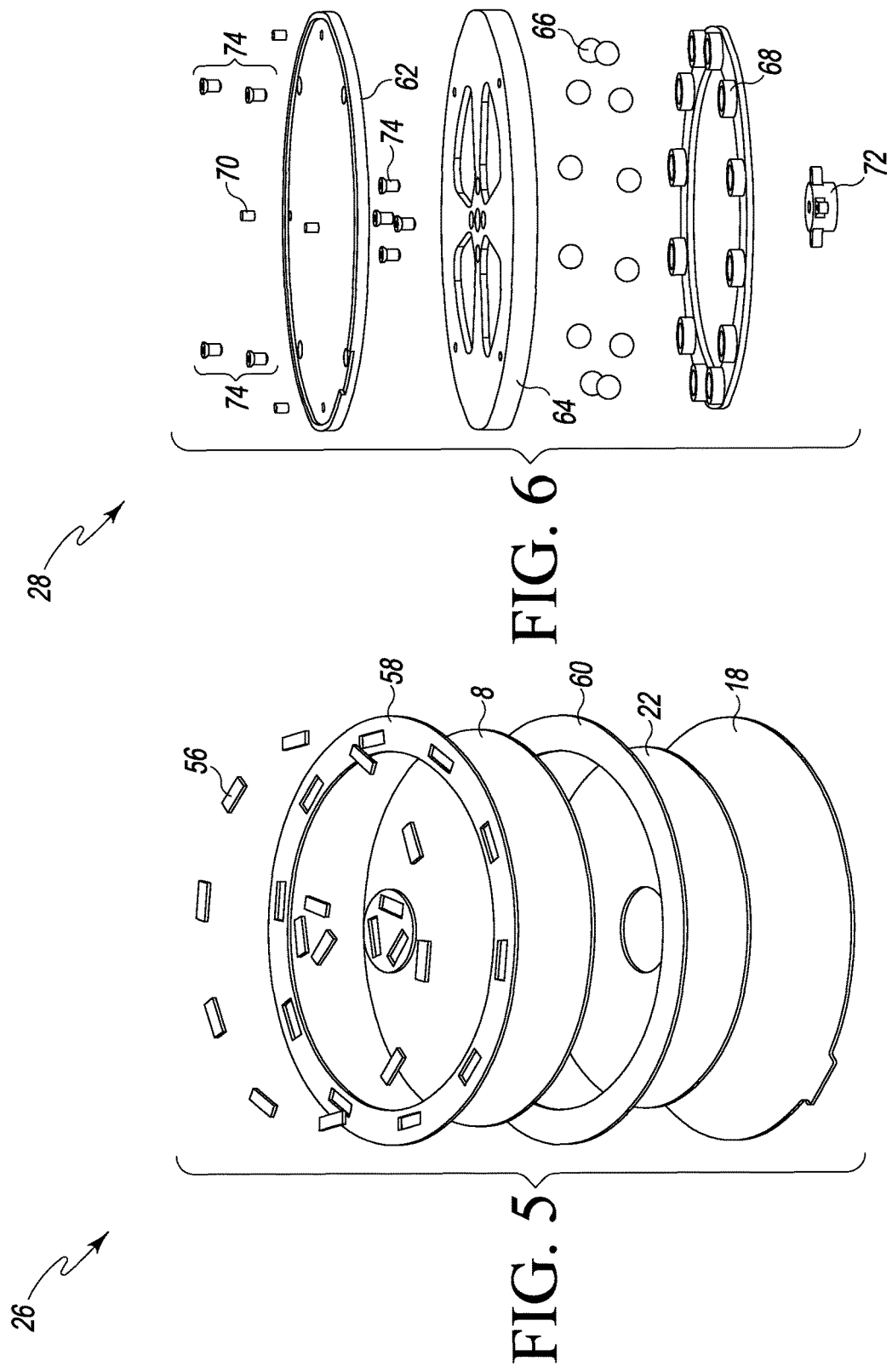

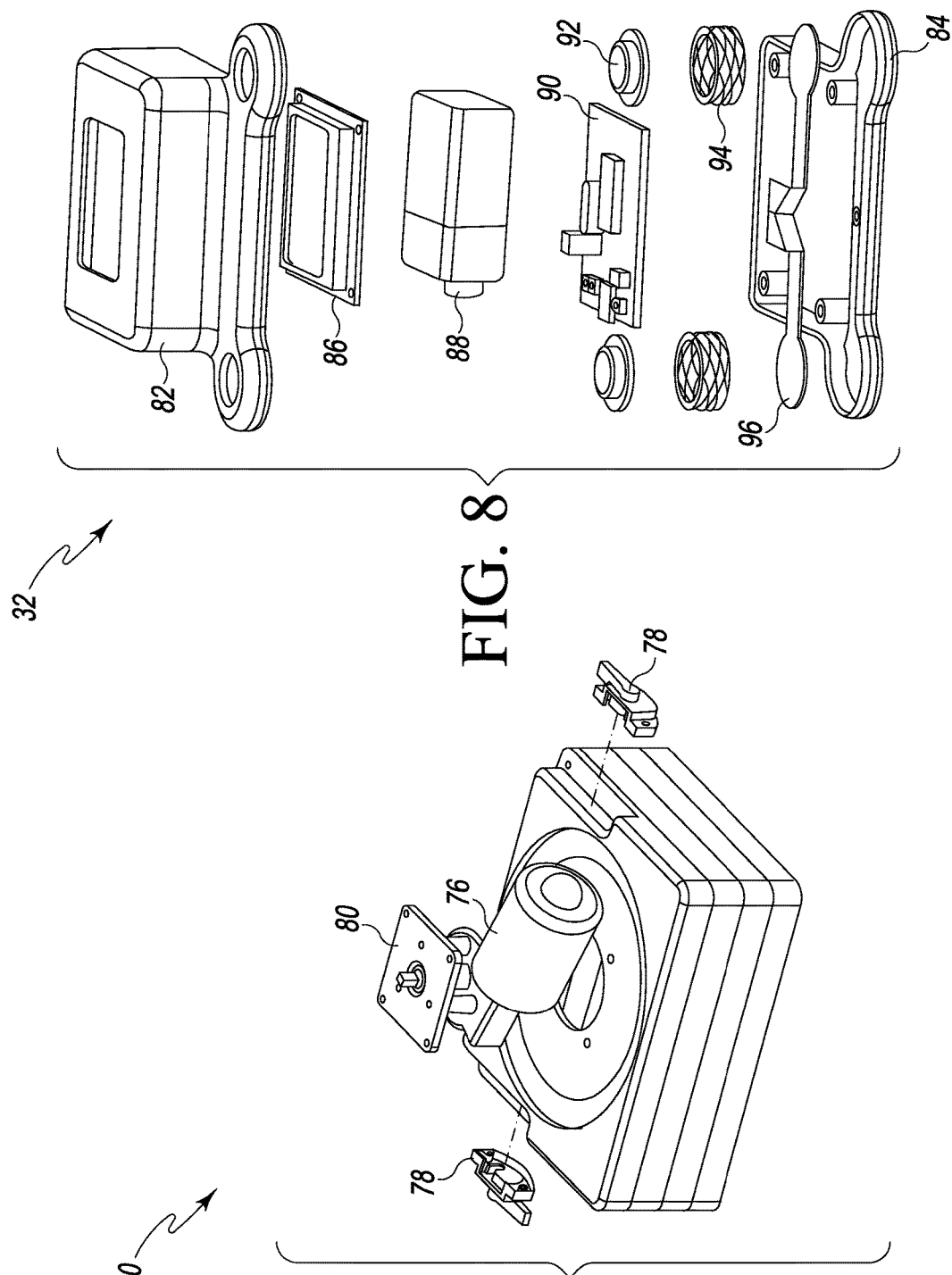

DEVICE FOR LARGE-SCALE MICROPARTICLE PRODUCTION AND METHOD OF USING THE SAME

RELATED APPLICATIONS

This application is a U.S. national stage entry under 35 U.S.C. §371(b) of PCT International Application No. PCT/US2014/041583, filed Jun. 9, 2014, and claims priority under 35 U.S.C. §119(e) to U.S. Provisional Application No. 61/832,297, filed Jun. 7, 2013, which both expressly incorporated by reference herein.

TECHNICAL FIELD

The present disclosure relates to a swiping device that may be used for dispensing drug-polymer solutions into a hydrogel mold or a polymer membrane mold comprising micro-cavities in order to enable large-scale production of microparticles, and the method of using said device.

BACKGROUND

Drug delivery systems have evolved over the last six decades. The current drug delivery technologies have produced numerous controlled release formulations in clinical use to improve patient compliance and convenience of use with reduced side effects. While significant advances have been made in drug delivery systems, improvements are needed, particularly to increase the time period of drug delivery.

Generally, oral drug delivery systems may deliver drugs for only a day. Transdermal formulations may often deliver drugs for up to a week or so. Implantable drug delivery systems may deliver drugs for longer periods of time, ranging from weeks to months. However, because surgical implantation of long-acting drug delivery systems is not preferred, the use of microparticle formulations that may be administered using a syringe has significant benefits. For this and other reasons, injectable formulations based on microparticles, also called or microdroplets, have been developed.

Generally, a microparticle is a solid particle having a size ranging from about 1 micrometer (μm) to about 100 μm. A microdroplet generally describes an emulsion particle having a size ranging from about 1 micrometer (μm) to about 100 μm. A microdroplet and a microparticle may comprise a solvent and solid content, and the solvent may be used to dissolve the solid content within the microparticle. Additionally, the sizes of a microparticle and a microdroplet (hereinafter referred to as a "microparticle") may be less than 1 μm or greater than 100 μm in size and may be known as a particle or a nanoparticle, respectively.

Most commercial microparticle formulations currently in clinical use have been prepared by double emulsion methods. A typical double emulsion method involves the initial dissolution of a drug in water (w) and subsequent emulsification of the drug in an organic solvent containing a biodegradable polymer. Organic solvents are referred to as oils (o). The process of emulsifying water droplets in an organic solvent is known as a water/oil (w/o) emulsion. When the stabilized w/o emulsion is placed into a larger container of water, a water/oil/water (w/o/w) double emulsion is created. The large amount of water is used to remove the organic solvent from the oil phase by extraction or by evaporation at elevated temperatures to allow the biodegradable polymer to harden. Thus, a double emulsion method is also called a double emulsion-solvent extraction or a double emulsion-solvent evaporation method.

The most commonly used biodegradable polymers for microparticle formulations are poly(lactic-co-glycolic acid) polymers, also called PLGA polymers. PLGA polymers may have different molecular weights or different Lactic:Glycolic or Lactide:Glycolide (L:G) ratios. Herein, the variety of PLGA polymers will be collectively referred to as "PLGA polymers" or simply "PLGA."

As previously described, only about a dozen injectable long-acting microparticle formulations have been commercially developed for clinical use to date as compared to the thousands of clinically developed oral controlled release formulations. Several factors are responsible for the highly limited development of injectable microparticle formulations, particularly, the limitations and disadvantages of the double emulsion methods used to produce microparticle formulations.

Large-scale production of microparticles is very difficult to achieve via a double emulsion method. Emulsification requires high speed mixing or stirring which is challenging when the volume becomes too large. The high speed stirring, required to break up emulsion particles or droplets into smaller particles or droplets, respectively, does not allow the resulting microparticles or microdroplets to be produced at specific sizes. More typically, a broad distribution of microparticle sizes is produced from double emulsion methods from which fractions containing larger particle sizes are typically removed because they are too big to administer to a patient via a syringe needle.

In addition, the viscosity of the polymer solution in an organic solvent used in the w/o/w double emulsion method cannot be high. More specifically, the concentration of PLGA polymers dissolved in organic solvent for making w/o/w double emulsion cannot be high. The use of low PLGA concentrations results in microparticles that may not have dense matrices and may not be able to control the drug release kinetics and drug delivery to the patient.

Double emulsion methods are also often insufficient to produce microparticles containing hydrophilic drugs, particularly microparticles containing highly water-soluble drugs or large biomolecules, such as proteins and genes. Protein drugs tend to undergo denaturation at the w/o interface, leading to inactivation of the drugs. Further, most microparticle formulations prepared by double emulsion methods show an initial burst drug release that is often about two to about three orders of magnitude higher than the subsequent steady state drug release. This extremely high initial drug burst release may cause or result in serious side effects to the patient.

Limitations of the double emulsion methods described herein have been, at least in part, hampering introduction of clinically useful microparticle formulations. Accordingly, there are great demands for developing new methods for making microparticles in industrial-scale amounts. Of particular interest are methods to produce industrial or large-scale quantities of microparticles comprising desirable properties, such as high drug loading, low initial burst release, control of size, and control of release kinetics and to also avoid many of the limitations and disadvantages of double emulsion methods.

In this regard, new methods have been developed that seek to provide more control over desirable properties such as high drug loading, particle size, and control of drug release kinetics. For example, microfluidic concentric nozzle method, flow-focusing method, micro dispenser method, membrane emulsification method, and nano- or micro-fabrication methods have been developed and tested. Nano- or micro-fabrication methods include nanoimprint lithography, solvent assisted micromolding, microfluid contact printing, microcontact hot printing, step and flash imprint lithography, and particle replication in nonwetting templates. While nano- and micro-fabrication methods of microparticle production do provide some improvements over double emulsion methods such as homogeneous particle size, these methods still have limitations in drug loading capacity, initial burst release, and steady state release. An additional limitation of micro-fabrication methods of producing microparticles is the inability to control or prevent formation of a scum layer.

A scum layer is formed on a mold or surface by leakage or escape of a solution used in the micro-fabrication process of making microparticles. For example, a solvent may be leaked from a drug-polymer solution onto a membrane or mold used during microparticle formation. The leaked solvent evaporates fast resulting in a solid scum layer on the surface of the mold or membrane.

Scum layer formation on molds or membranes is a major disadvantage of micro-fabrication methods of producing microparticles. A scum layer on a mold or membrane results in unwanted loss of microparticles and drug-polymer solutions, since individual microparticles are connected to the scum layer and cannot be separated from it by agitation, sonication, or filtration. For example, formation of a scum layer during large-scale production of microparticles results in reduced microparticle yields which may be less than about 70% of the starting material.

Additionally, large-scale production of microparticles possessing such properties as controlling scum formation, drug loading capacity, initial burst release, and steady state release is still very difficult. For example, a major disadvantage of previous large-scale microparticle production processes was that the micro-cavities of the molds were manually filled with a drug-polymer mixture, which made the process rather slow and of low yields. Therefore, to manufacture industrial or large-scale quantities of drug-polymer microparticles or to scale-up the microparticle production process efficiently using polymer membrane or hydrogel mold, a swiping device and method for using the same has been developed as described herein.

SUMMARY OF THE INVENTION

The present disclosure is directed to a device for production of microparticles that comprises an upper assembly that further comprises an upper top portion, an upper bottom portion, and a blade; a middle assembly that further comprises a middle top portion, a middle bottom portion, and a plate; and a lower assembly that further comprises a lower top portion, a lower bottom portion, and a motor. The upper bottom portion of the upper assembly is secured to the middle top portion of the middle assembly and the middle bottom portion of the middle assembly is secured to the lower top portion of the lower assembly. The plate of the middle assembly is rotated directly under the blade by the motor, and the solution is directly applied from the blade onto the plate.

The lower assembly of the device may further comprise a vacuum motor. The upper assembly may further comprise a set of arms to raise the upper assembly or at least one crossbar to secure the blade onto the upper assembly. The middle assembly may further comprise a disk that is secured to the plate. The disk may be made of rubber, plastic, or metal and may be secured to the plate by a plurality of means, for example, a steel ring, an O-ring, or tape.

Additionally the middle assembly may further comprise a plurality of ball bearings, a ball bearing plate, and a ball bearing race ring that are secured to the motor to rotate the plate. The middle assembly may also comprise a mold. The mold may be made of gelatin or PVA and may have a size ranging from about 9 cm to about 21 cm. The mold may be secured to the plate by magnets. Further, a cushion plate may lie between the mold and the disk on the device.

The device of the present disclosure may comprise a blade comprising one or more portals. The portals may be located in the center or on the right side of the blade. The portals may be connected to one or more channels and one or more reservoirs within the blade. The one or more reservoirs may have a triangular shape. Additionally, the portals may comprise a plug. The blade may further comprise several features including a dovetail design and an air vent.

Finally, the present disclosure is also directed to a method of using the device, wherein the method comprises placing a mold on the plate of the device, introducing a solution to the blade of the device, placing the blade on the device, lowering the blade to the mold, rotating the mold and the plate under the blade, dispensing the solution from the blade onto the mold, stopping the mold on the rotating plate, removing the mold filled with solution, drying the mold, wherein drying the mold hardens the solution to produce microparticles, and releasing the microparticles after the drying step.

BRIEF DESCRIPTION OF THE DRAWINGS

Embodiments of the present disclosure will now be described by way of example in greater detail with reference to attached figures, in which:

FIG. 5 is an exploded view of an upper platter assembly component of the swiping device of FIG. 3C.

FIG. 6 is an exploded view of a lower platter assembly component of the SpinSwiper device of FIG. 3C.

FIG. 7 is a partially exploded view of a lower base assembly component of the SpinSwiper device of FIG. 3C.

FIG. 8 is an exploded view of a pressure sensor component of the swiping device of FIG. 3C.

DETAILED DESCRIPTION

Figure 1:
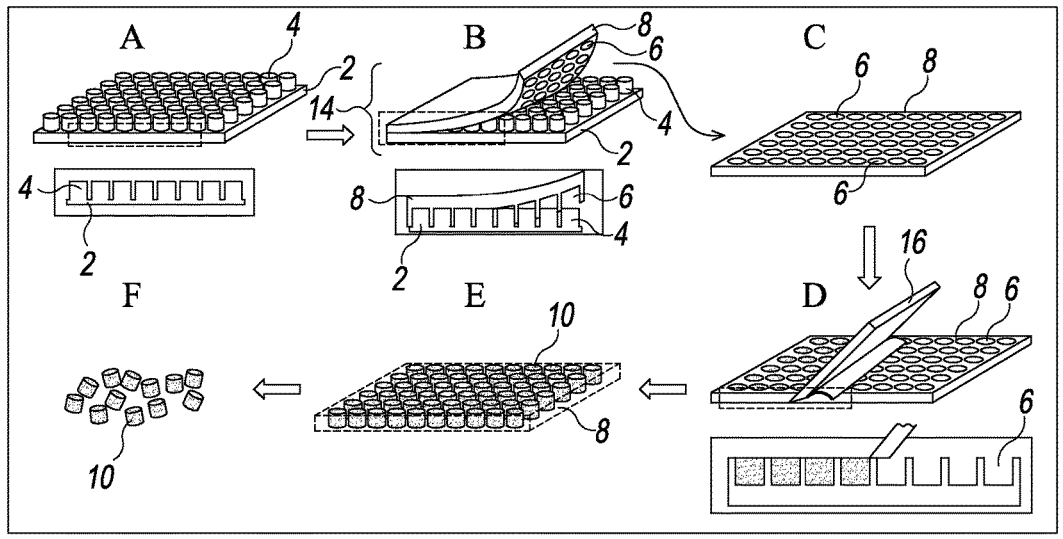
FIG. 1 is a schematic of a hydrogel mold method of microparticle production.

While the concepts of the present disclosure are susceptible to various modifications and alternative forms, specific exemplary embodiments thereof have been illustrated by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

While generally, nano- and micro-fabrication methods of microparticle formulation produce homogeneous microparticles, most are unable to consistently produce large quantities of microparticles having reproducible properties. The semi-automated swiping device described (hereinafter referred to as "the device") and methods to use the device enable large-scale production of microparticles with uniformity of predefined shapes and sizes and minimization or prevention of a scum layer formation, which are two illustrative and advantageous features over previous microparticle production methods.

Figure 2:
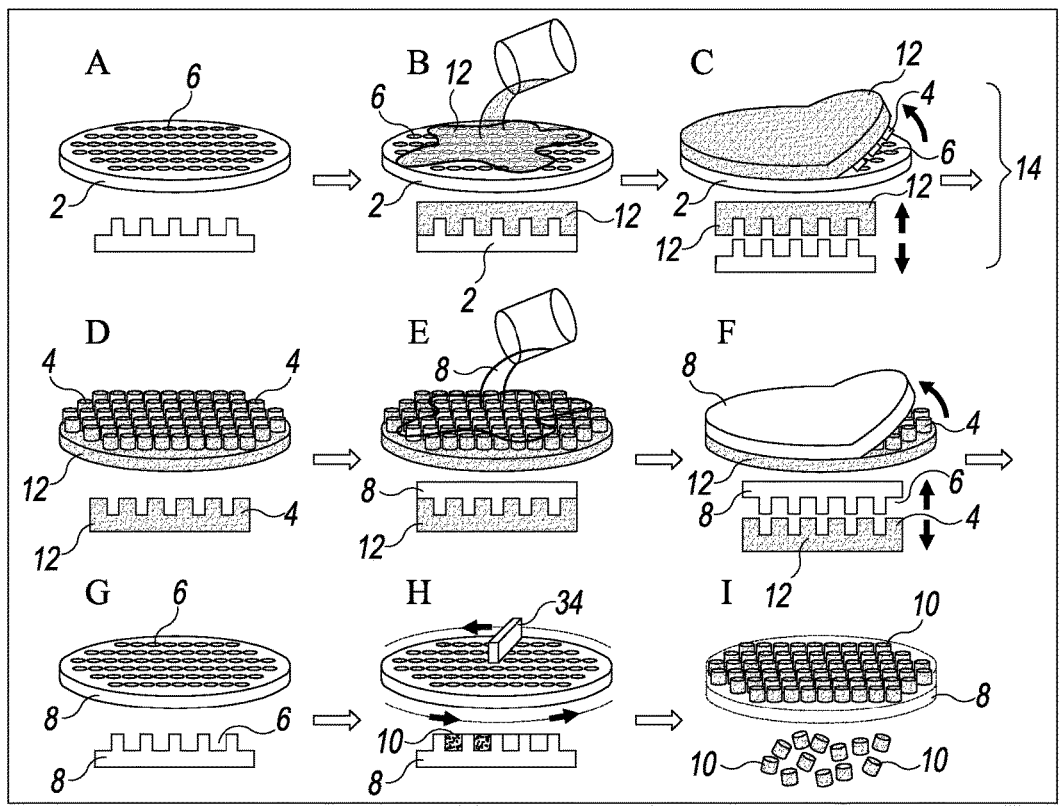
FIG. 2 is a schematic of a dry polymer membrane mold method of microparticle production.

The present microparticle (10) production process (see FIG. 1) comprises using a template (2) and a hydrogel mold (8) or a polymer membrane mold (8) as depicted in FIGS. 1 and 2, respectively. Referring now to FIGS. 1A and 2A, a silicon wafer master template (2) may be prepared by UV lithography to comprise micro-pillars (4) and micro-cavities (6), respectively. The size of a micro-pillar (4) or a micro-cavity (6) in a silicon wafer master template (2) and the size of a micro-pillar (4) in an intermediate template (12) directly corresponds with the size of a resulting microparticle (10) prepared from the templates (2 and 12).

The diameter of a micro-pillar (4) or a micro-cavity (6) which dictate the size of a microparticle (10), may be any specific value of interest ranging from about 1.5 µm to about 100 µm or greater than 100 µm, such as about 200 µm, 300 µm, 400 µm, and 500 µm. Alternatively, microparticles (10) requiring a diameter less than about 1.5 µm and of submicron size may be obtained using templates (2 or 12) prepared by electron-beam lithography. For example, microparticles (10) of about 1 µm to about 1.5 µm or about 0.5 µm to about 1.5 µm may be prepared by electron-beam lithography. Typically, microparticles (10) of about 50 µm are preferred, because they are small enough for easy injection using common syringe needles, but large enough to serve as a drug reservoir for long-term drug delivery.

More specifically, the diameter of a micro-pillar (4), a micro-cavity (6), or a microparticle (10) of the present disclosure may range from about 1.5 µm to about 90 µm, from about 1.5 µm to about 80 µm, from about 1.5 µm to about 70 µm, from about 1.5 µm to about 60 µm, from about 1.5 µm to about 50 µm, from about 1.5 µm to about 40 µm, from about 1.5 µm to about 30 µm, from about 1.5 µm to about 20 µm, and from about 1.5 µm to about 10 µm. The diameter of a micro-pillar (4), a micro-cavity (6), or a microparticle (10) may also be greater than about 100 µm, from about 10 µm to about 100 µm, from about 10 µm to about 90 µm, from about 10 µm to about 80 µm, from about 10 µm to about 70 µm, from about 10 µm to about 60 µm, from about 10 µm to about 50 µm, from about 10 µm to about 40 µm, from about 10 µm to about 30 µm, and from about 10 µm to about 20 µm. Additionally, the diameter of a micro-pillar (4), a micro-cavity (6), or a microparticle (10) may be from about 20 µm to about 60 µm, from about 30 µm to about 60 µm, from about 35 µm to about 65 µm, from about 40 µm to about 60 µm, from about 40 µm to about 50 µm, from about 45 µm to about 55 µm, from about 48 µm to about 52 µm, from about 49 µm to about 51 µm, from about 49.5 µm to about 50.5 µm, from about 50 µm to about 100 µm, from about 50 µm to about 90 µm, from about 50 µm to about 80 µm, from about 50 µm to about 70 µm, and from about 50 µm to about 60 µm.

Referring now to FIG. 1, microparticle (10) production may begin with a solution that can form a gel (8), a mold (8), or membrane (8) after being applied on top of a master template (2). Gelatin may be used to form a hydrogel mold (8). An illustrative polymer solution is poly(vinyl alcohol), also called PVA, which may also be used to form a membrane (8). Mold imprinting occurs when a polymer solution that may be dried or cooled to form a membrane (8) or a gel (8), for example, PVA or gelatin, is applied on top of a silicon master template (2, see FIG. 1B) to form a polymer-template construct (14) or a gelatin-template construct (14), respectively.

The temperature of the gelatin-template construct (14) or the polymer-template construct (14) may be decreased or increased, respectively, to form a mold (8, see FIG. 1C). For example, a gelatin-template construct (14) may cure to form a hydrogel mold (8) at a temperature from about 1° C. to about 4° C., from about 2° C. to about 4° C., from about 1° C. to about 3° C., from about 2° C. to about 3° C., from about 1.5° C. to about 3.5° C., from about 2.5° C. to about 3.5° C., from about 3.5° C. to about 4° C., and at about 4° C. The gelatin-template construct (14) may cure for a time period of about two hours to about four hours, about two hours to about three hours, and from about three hours to about four hours.

Additionally, a polymer-template construct (14) may be cured to form a polymer membrane (8) at ambient or room temperature (e.g., about 26° C.) for about six hours to about twelve hours, from about six hours to about ten hours, from about eight hours to about eleven hours, and from about seven hours to eleven hours. Air bubbles on the surface of a polymer mold (8) (e.g., PVA) may result in substandard microparticle (10) production due to their ability to induce formation of a scum layer on the polymer membrane (8) surface. Drying the PVA mold (8) at ambient temperatures may advantageously result in the prevention of air bubble formation on the surface of the membrane (8), and thus prevent formation of a scum layer. Alternatively, a PVA mold (8) may be cured in less time, for example, from about two hours to about six hours, if cured at temperatures above ambient temperatures (e.g., about 60° C.).

After drying, the hydrogel (8) or polymer membrane mold (8) is separated from the silicon master template (2) of the gelatin-template construct (14) or polymer-template construct (14), respectively, and placed on a flat surface to expose the micro-cavities (6, see FIG. 1C). The micro-cavities (6) may be filled with a drug-polymer mixture using a spreader (16, see FIG. 1D). Microparticles (10) are released from the micro-cavities (6) of the hydrogel mold (8) by dissolving the membrane (8) in water or a mixture of water and an organic solvent and collecting the microparticles (10) for subsequent use (see FIGS. 1E and 1F).

Referring now to FIG. 2, to preserve the silicon wafer master template (2), many copies of intermediate templates (12) may be made. An intermediate polymer template (12) of a silicon wafer master template (2) may be comprised of poly(dimethylsiloxane), also called PDMS or silicone rubber (12, see FIG. 2B), which is a water-insoluble polymer. Intermediate polymer templates (12) are formed by pouring the polymer solution (e.g., PDMS) onto the silicon wafer master template (2, see FIG. 2B) to form a polymer-template construct (14, see FIG. 2C). The PDMS template (12) cures on the silicon wafer master template (2) of the polymer-template construct (14) for a time period ranging from about two hours to about six hours, from about three hours to about five hours, from about four hours to about six hours, from about two hours to about five hours, and from about three hours to about six hours. Additionally, the PDMS template (12) cures at a temperature ranging from about 20° C. to about 65° C., from about 58° C. to about 62° C., from about 59° C. to about 61° C., and at about 60° C.

The PDMS template (12) is then separated from the silicon wafer master template (2), (see FIG. 2C) of the polymer-template construct (14). The PDMS template (12) comprises micro-pillars (4) instead of micro-cavities (6) as found in the original silicon wafer master template (2). The PDMS template (12) is placed upside down on a flat surface to expose the micro-pillars (4, see FIG. 2D).

A polymer solution may be added to the top of the silicone rubber template (12) and dried to form a membrane (8) or a gel (8, see FIG. 2E), such as a polymer membrane mold (8, see FIG. 2F). Polymers, such as PVA and other water-soluble polymers, may be used to make membrane molds (8) that are durable, resilient, and easy-to-handle. Other polymers may also be used, for example, polymers that may be dissolved in water or solvent and that may be dried to form a membrane (8) or a gel (8). For example, ethylcellulose is a water-insoluble polymer that may be dissolved in an organic solvent, or disperse in water, to form a membrane (8) or a gel (8) and therefore, may be used to form a polymer membrane mold (8) of the present disclosure.

As previously described, a polymer-template construct (14) may be cured to form a resilient polymer membrane (8) at ambient or room temperature (e.g., about 25° C.) from about six hours to about twelve hours. Drying the PVA polymer mold (8) at ambient temperatures may advantageously result in the prevention of air bubble formation on the surface of the membrane (8), and thus prevent formation of a scum layer. Alternatively, a PVA mold (8) may be cured in less time, for example from about two hours to about six hours, if cured at temperatures above ambient temperatures (e.g., about 60° C.). Microparticles (10) are released from the micro-cavities (6) of the polymer mold (8) by dissolving the membrane (8) in water or an organic solvent and collecting the microparticles (10) for subsequent use (see FIG. 2I).

The polymer membrane mold (8) is removed, such as by peeling away the mold (8) from the silicone rubber template (12, see FIG. 2F) and placed on a flat surface exposing the micro-cavities (6, see FIG. 2G). The micro-cavities (6) may be manually filled with a drug-polymer mixture using a spreader (16) or may be semi-automatically filled with the drug-polymer mixture when placed on a device (20 and 100) of the present disclosure. In some device embodiments, the drug-polymer mixture is added to the polymer mold (8) using a blade component (34), as shown in FIG. 2H.

One advantage of the hydrogel and polymer mold (8) methods of producing microparticles (10) is the ease of collecting of the microparticles (10) formed in the membrane (8). Drug-polymer microparticles (10) may be released from the micro-cavities (6) of the hydrogel (8) and polymer membrane molds (8) by dissolving the membranes (8) in water or a mixture of water and an organic solvent (see FIGS. 1E and 2I). The released drug-polymer microparticles (10) may be washed and collected by centrifuging or filtering through fine meshes.

The drug-polymer mixture loaded into a hydrogel mold (8) may comprise various polymers, including poly(lactic-co-glycolic acid), also called PLGA. Different molecular weights and Lactide:Glycolide (L:G) ratios of PLGA polymers may also be used to mix with a drug and prepare microparticles (10) of the present disclosure. For example, the L:G ratio of polymers, such as PLGA, is not limited and may vary in order to produce polymers with different properties such as, degradation time, degree of crystallinity, etc. However, generally, the L:G ratio of a polymer used in a drug-polymer mixture may range from about 50:50 to about 95:5, including about 75:25.

A drug or drugs of the drug-polymer mixture, are not limited, and may include drugs as are understood in the art, such as low molecular weight hydrophobic molecules (e.g., risperidone, triamcinolone, doxycycline, naltrexone, ritonavir, paclitaxel, lidocaine, and dexamethasone), hydrophilic molecules (e.g., acetazolamide, ciprofloxacin, aspirin, and acetaminophen), high molecular weight peptides (e.g., triptorelin, goserelin, leuprolide, octreotide, capreomycin, and exenatide), proteins (e.g., growth hormones and antibodies), and nucleic acid molecules (e.g., deoxyribonucleic acids and ribonucleic acids). The present drug-polymer mixture may be prepared using about 1% to about 60% of the drug and about 0% to about 99% of the polymer in the drug-polymer mixture. More specifically, from about 1% to about 10%, from about 10% to about 60%, from about 20% to about 50%, from about 25% to about 50%, from about 5% to about 25%, from about 10% to about 50%, from about 30% to about 60%, from about 40% to about 55%, and about 50% of total drug weight percent may be used in the present drug-polymer mixture.

Additionally, from about 2% to about 10%, from about 10% to about 40%, from about 20% to about 50%, from about 25% to about 50%, from about 5% to about 25%, from about 10% to about 50%, from about 30% to about 50%, from about 10% to about 45%, and about 50% of total polymer weight percent may be used in the present drug-polymer mixture. The drug-polymer mixture is dissolved in an organic solvent to prepare the drug-polymer solution that is loaded into the micro-cavities (6) of both hydrogel (8) and polymer membrane molds (8). The drug-polymer solution comprises from about 1% to about 95% total weight percent of solvent. Organic solvents, such as DCM, n-butyl acetate, dioxane, and mixtures of different solvents may be employed for dissolution of the drug-polymer composition 404.

Hydrogel (8) or polymer molds (8) comprising micro-cavities (6) may be made in a predetermined size. For preparation of microparticles (10), one example of a rubber disk (22) size may be about four inches in diameter, such that the mold comprises a size that may range from about 7 centimeters (cm) to about 10 cm, and generally about 7 cm. However, semi-automation of the microparticle (10) production process allows larger mold sizes (e.g., about eight inches in diameter) to be utilized. An eight-inch mold may comprise a size that ranges from about 17 cm to about 20 cm, from about 18 cm to about 20 cm and generally about 19 cm. Additionally, templates (2 and 12) and molds (8) used on the instant device may incorporate various shapes to produce geometric microparticles (10), including microspheres, microrings, micropacmans, microtriangles, microstars, microcrosses, and microdiamonds.

Swiping, as used herein, is the act of applying a solution to a moving mold (8) that is powered by a mechanical means (i.e., a motor), such that the act of solution application is semi-automated. Referring now to FIGS. 3-17, various embodiments of a swiping device of the present disclosure are illustrated. One embodiment of the swiping device comprises a vacuum component (100, hereinafter referred to as the "vacuum device") while another embodiment of the swiping device does not comprise a vacuum component (20, hereinafter referred to as the "device").

Figure 3:
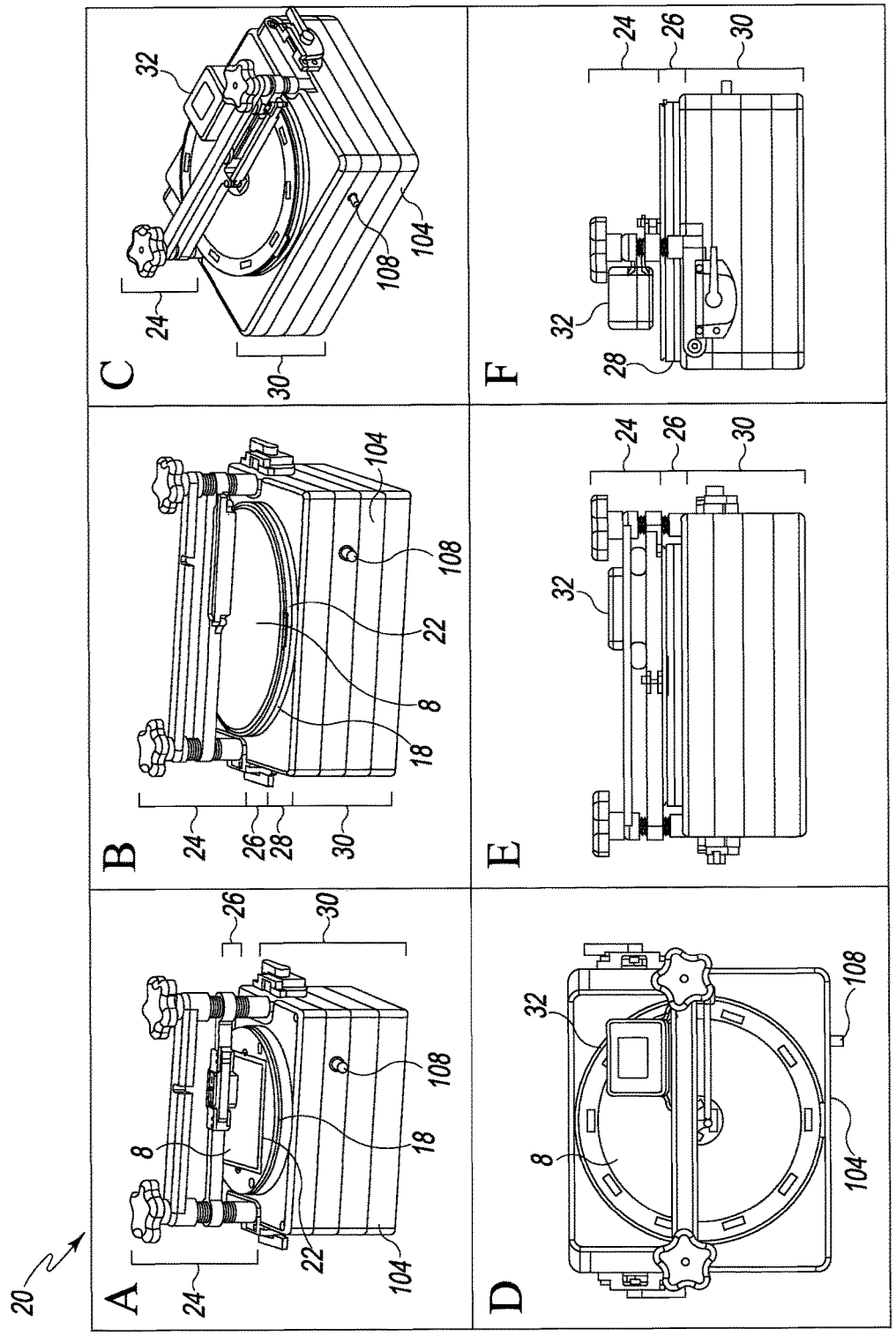
FIG. 3A is a perspective view of one embodiment of a swiping device featuring a four-inch rotating plate.
FIG. 3B is a perspective view of the swiping device embodiment of FIG. 3A featuring an eight-inch rotating plate.
FIG. 3C is a perspective view of the swiping device embodiment of FIG. 3B featuring a pressure sensor component.
FIG. 3D is a plan view of the swiping device of FIG. 3C.
FIG. 3E is a back elevation view of the swiping device of FIG. 3C.
FIG. 3F is a side elevation view of the swiping device of FIG. 3C.

A swiping device of the present disclosure (20 and 100) is a semi-automated machine. One embodiment of the swiping device (20) shown in FIG. 3 is semi-automated with a four-inch circular, rotating plate or turntable (18), as shown in FIG. 3A. Another embodiment of the device (20) may comprise an eight-inch rotating plate (18) as shown in FIG. 3B. The rubber template base (22) at the center of the device is rectangular in shape for the four-inch plate (18) and circular for the eight-inch plate (18, see FIGS. 3A and 3B, respectively). As compared to the four-inch device (20) of FIG. 3A, the eight-inch device (20) of FIG. 3B requires higher motor torque which is necessary for increased smoothness of the membrane (8) and rotating a larger plate (18). The power and speed of the plate (18) rotation on the device (20) is controlled by a knob (108) on the front panel (104) of the device (see FIGS. 3A-3C).

Various views of the device (20) are shown in FIGS. 3A-3F. As shown in FIGS. 3A-3B, a device (20) includes: 1) an upper or blade assembly (24), 2) a middle assembly comprising an upper platter assembly (26) and a lower platter assembly (28), and 3) a lower or base assembly (30). As seen in FIGS. 3A-3F, the upper assemblies (24 and 26) and the lower platter assembly (28) are connected to the base assembly (30) using a set of locks (78). Each set of locks (78) is located on a side panel of the base assembly (30) of the device (20). An optional pressure sensor component (32) of a device (20) is also shown in FIGS. 3C-3F.

Figure 4:
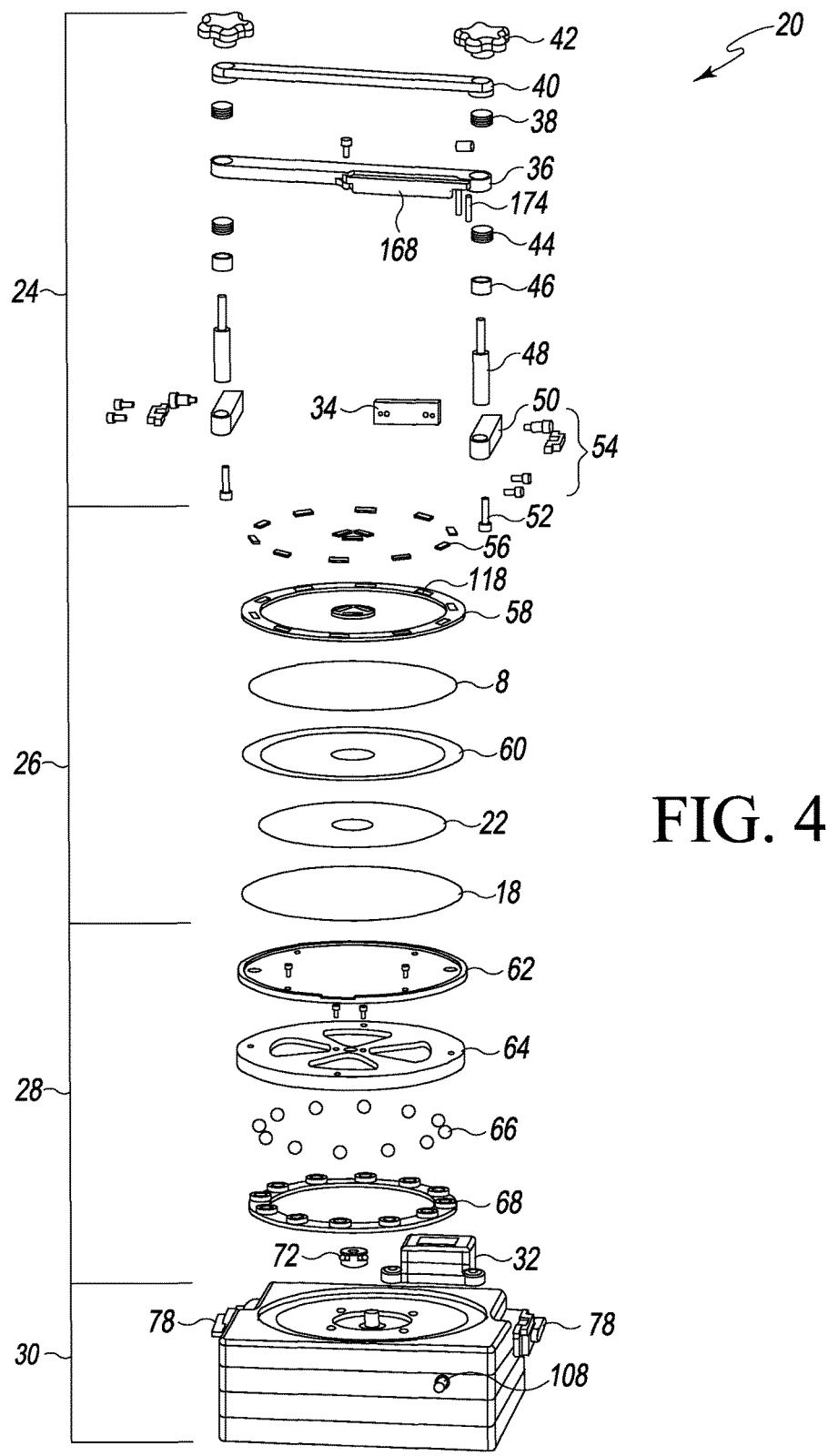
FIG. 4 is an exploded view of the swiping device of FIG. 3C.

Referring now to FIG. 4, an exploded view of a device (20) is shown. The upper platter assembly (26) of the device (20) is designed to have a circular backing plate (18) in the center which may be made out of plastic or a metal, such as aluminum or stainless steel. The circular backing plate (18) is made to rotate while a drug-polymer solution is introduced to the plate (18) by a swiping blade (34). The backing plate (18) also provides a surface for attaching a rubber disk (22) upon which a membrane (8) is located. A swiping blade (34) of the upper assembly (24) contains a solution that may be distributed and applied to the membrane (8) via a swiping method described herein. The blade (34) may be secured onto a bottom crossbar (36) which holds the blade (34) in the upper assembly (24) with a latch (168) and one or more pins (174).

Directly above the bottom crossbar (36) on the upper assembly (24) are springs (38) that support a top crossbar (40). The top crossbar (40) distributes pressure generated from a set of knobs (42). The knobs (42) are manually turned to raise and lower the top crossbar (40), the bottom crossbar (36), and the blade (34).

Another set of springs (44) absorb upward force from the blade (34) when it is in contact with the membrane (8). Cylinders (46) provide a solid surface for the springs (38 and 44) to rest on such that the height of the crossbars may be adjusted. Components 36-46 are anchored by a set of threaded dowels (48). The threaded dowels (48) are attached to arms (50) by screws (52). The arms (50) are also attached to a base assembly (30) of the device (20). The arms (50) allow the upper assembly (24) to be vertically rotated up to 180° C. for easy insertion and removal of the membrane (8, see FIG. 17H). Upper locks (54) are attached to the sides of the arms (50) to secure the upper assembly (24) to the base (30) during swiping.

The upper platter assembly (26) of the device (20) is shown in FIG. 4 and in the larger exploded view of FIG. 5. The upper platter assembly (26) is responsible for securing the membrane (8) to the device (20). Different methods of securing the membrane (8) to the device (20) may be used. In the illustrative embodiments (see FIGS. 4 and 5), the membrane (8) is secured by magnets (56). The magnets (56) secure the membrane (8) onto a magnet ring (58) such that the magnets (56) are secured to a metal ring (60). The metal ring (60) provides a surface for the magnets (56) to attach the membrane (8) to the device (20). The metal ring (60) may be comprised of aluminum or stainless steel and also secures the rubber disk (22) onto the backing plate (18) such that the PVA membrane (8) is placed on the backing plate (18) with the metal ring (60) and the rubber disk (22). The magnet ring (58) is then placed over the metal ring (60) to secure the PVA membrane (8).

The magnet ring (58) may comprise a plurality of slots (118) to accommodate the magnetic bars (56) that secure the membrane (8) to the metal ring (60). In an alternate embodiment, the PVA membrane (8) may be secured to the backing plate (18) using a circular clamp. The clamp fits in a groove cut out of the backing plate (18). In another embodiment, the PVA membrane (8) may be secured to the plate (18) by an O-ring that is inserted into a channel on the backing plate (18). In another embodiment, the PVA membrane (8) may be secured to the device (20) using double sided tape.

The lower platter assembly (28) comprises a cover plate (62) which connects the upper assemblies (24 and 26) to the base assembly (30). The lower platter assembly (28) also holds and rotates the membrane (8), the rubber disk (22), and the backing plate (18). A ball bearing plate (64), ball bearings (66), and a ball bearing race ring (68) ensure that rotation of the membrane (8), the rubber disk (22), and the backing plate (18) is smooth and uniform. Finally, the lower base assembly (30) supports the lower platter assembly (28) and upper assemblies (24 and 26) of the device (20) which are connected to the base assembly (30) by a lock (78) on each side of the device (20, see FIGS. 3B and 4). In addition, the lower base assembly (30) houses the power supply (76, e.g., a motor) and comprises one or more knobs (108) in order to adjust the speed of rotation of the membrane (8).

In a device (20), the upper platter assembly (26) of FIG. 5 is placed on the lower platter assembly (28) of FIG. 6. The lower platter assembly (28) is the portion of the device (20) shown in FIGS. 3 and 4 that rotates. When the upper platter assembly (26) is placed on the lower platter assembly (28), the membrane (8) is then rotated under the swiping blade (34) and the upper assembly (24) while the solution is being dispensed. The lower platter assembly (28) is contained atop of the base (30) on the device (20).

Referring now to FIG. 6, the lower platter assembly (28) comprises a cover plate (62) that allows access to the base assembly (30, see FIG. 4) of the device (20) when removed by removing screws (74). The cover plate (62) is the foundation upon which the upper platter assembly (26) sits and also provides support for the backing plate (18). The cover plate (62) may also be leveled or balanced using set screws (70).

Directly below the cover plate (62) is a ball bearing plate (64) which covers the ball bearings (66). The set screws (70) allow for level adjustment between the cover plate (62) and the ball bearing plate (64). The ball bearing plate (64) covers a plurality of ball bearings (66) and a ball bearing race ring (68) that houses the ball bearings (66). The ball bearings (66) ensure smooth and level rotation of the plate (18) by reducing friction and bearing load from the upper assembly (24). The ball bearing plate (64) is attached to the motor assembly (76) of the base (30) by screws (74) connected to the rotating shaft (72) and the shaft base (80), see FIG. 7). The shaft (72) and the shaft base (80) provide the movement for the rotation from the motor (76) to the lower platter assembly (28).

Referring now to FIG. 7, the lower assembly (30) serves as the base (30) of the device (20), as shown. The shaft (72) in the lower platter assembly (28) attached to the shaft base (80) and is mechanically powered by a motor (76). The lower locks (78) secure the upper assembly (24, see FIG. 4) onto the base (30) during swiping. The base (30) houses the motor (76), the lower platter assembly (28), and all electrical components (e.g., wiring, etc.). The movement of the device (20, see FIG. 4) is started, stopped, and the speed is adjusted by a knob (108) at the front of the base (30) of the device (20).

A pressure sensor (32) may be used with a device (20) or a vacuum device (100). Referring back to FIGS. 3 and 4, the eight-inch device (20) of FIG. 3B is shown with the additional pressure sensor component (32) attached to the base (30) in FIGS. 3C-3F. A pressure sensor (32) may also be added to a four-inch device (20). As particularly shown in FIGS. 3E and 3F, the pressure sensor (32) may be inserted between the top crossbar (40) and the bottom crossbar (36) of the upper assembly (24).

Referring now to FIG. 8, the pressure sensor (32) is contained within an upper housing (82) and a lower housing (84) that each contains various components of the sensor (32). An LCD screen (86) displays pressure values of the device (20). A battery (88) provides power for the pressure sensor (32).

A microprocessor control board (90) converts the pressure sensor (32) information to values displayed on the LCD screen (86). Plungers (92), which are placed on top of wave springs (94), may be compressed to allow the pressure sensor (32) to fit between the top crossbar (40) and the bottom crossbar (36). As the knobs (42) are turned on the device (20), the top crossbar (40) lowers, and the plungers (92) of the microprocessor control board (90) are compressed. Wave springs (94) absorb pressure from the plungers (92) and distribute the pressure evenly over the pressure sensor (32). A set of sensors (96) sit directly below the wave springs (94) and measure the pressures exerted from the springs (94). Values displayed on the LCD screen (86) allow an operator to ensure that the pressure remains consistent from membrane (8) to membrane (8).

Another optional component for the upper assembly (24) of the device (20) or the vacuum device (100) may be a cleaning blade. Solvent may be introduced through a cleaning blade during or after swiping to further improve yield and efficiency of microparticle (10) production. Referring back to FIG. 4, the cleaning blade may be attached to the bottom crossbar (36) as a mirror image of the swiping blade (34). Organic solvent may be pumped through tubing (160) into the swiping blade (34) using a syringe pump (166) or any instrument that may deliver the solvent in a controlled manner (see FIG. 17).

Alternatively, a vacuum embodiment of the instant device (100) is a semi-automated machine for dispensing drug-polymer solution into micro-cavities (6) of a polymer mold (8) to create microparticles (10), a process otherwise called swiping. The vacuum device (100) is also designed to enable scale-up production and to expedite formation of microparticles (10) by incorporating a vacuum suction. A dried, polymer mold, such as a PVA membrane (8), may be a more durable mold, and is preferred over a hydrogel mold (8) with use of a vacuum device (100).

Figure 9:
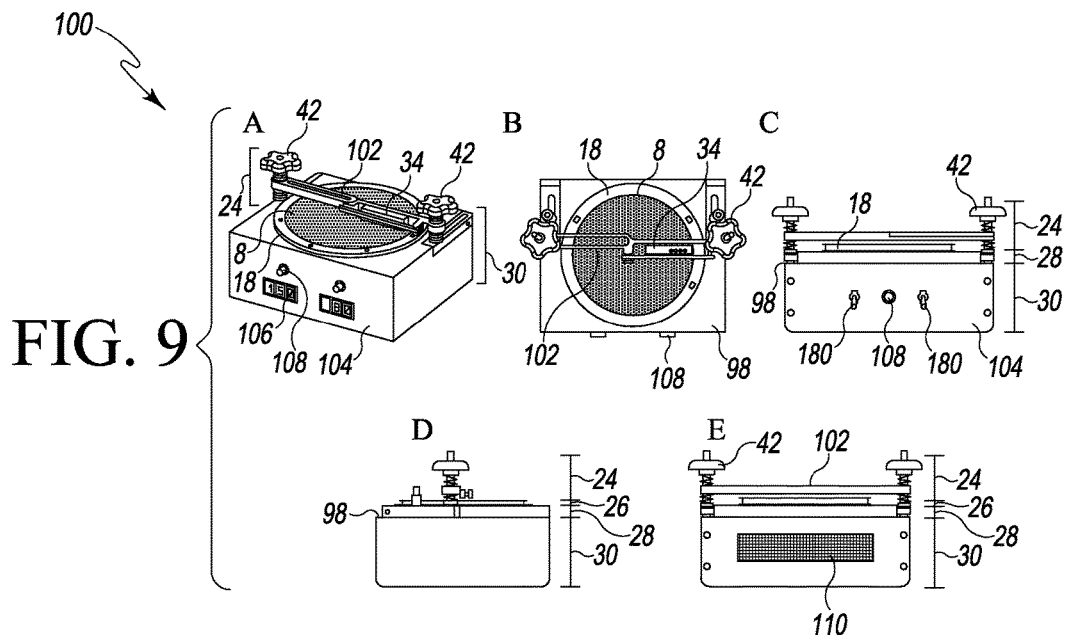
FIG. 9A is a perspective view of a second embodiment of a swiping device comprising a vacuum with a top blade assembly, a middle vacuum platter assembly, and a bottom base assembly.
FIG. 9B is a plan view of the swiping device of FIG. 9A.
FIG. 9C is a front elevation view of the swiping device of FIG. 9A.
FIG. 9D is a side elevation view of the swiping device of FIG. 9A.
FIG. 9E is a back elevation view of the swiping device of FIG. 9A.
Figure 10:
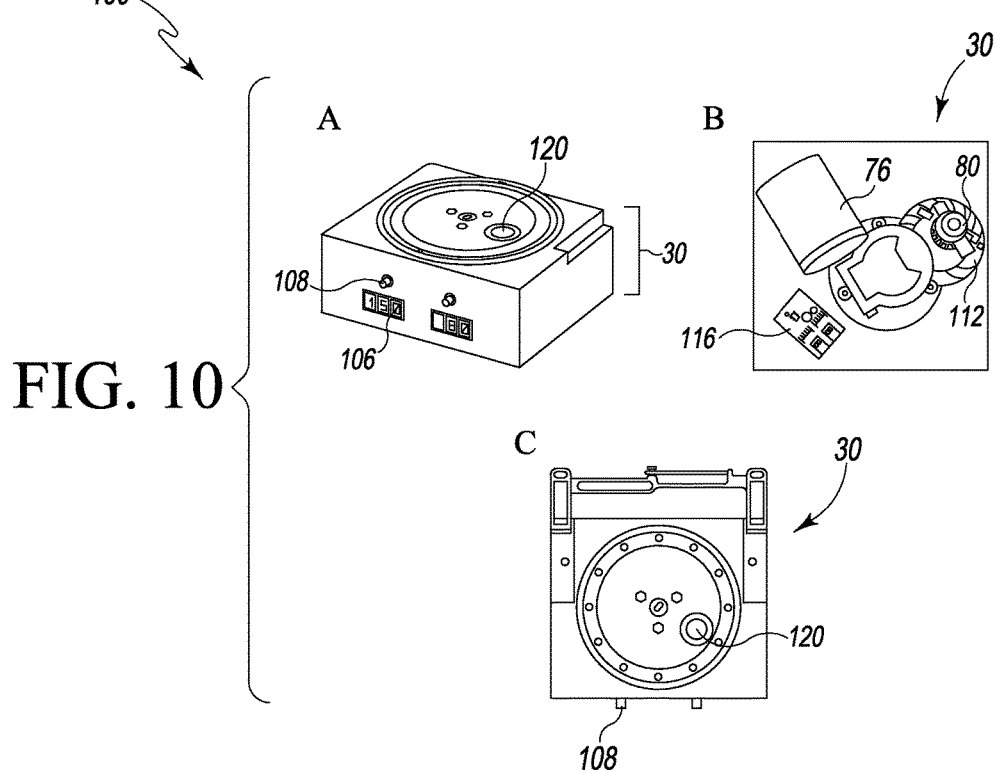
FIG. 10A is a perspective view of a base assembly of the swiping device of FIG. 9A.
FIG. 10B is an inside view of the base assembly of the swiping device of FIG. 9A.
FIG. 10C is a plan view of the base assembly of the swiping device of FIG. 9A with a base assembly open, a vacuum platter assembly absent, and further comprising a vacuum line.
Figure 11:
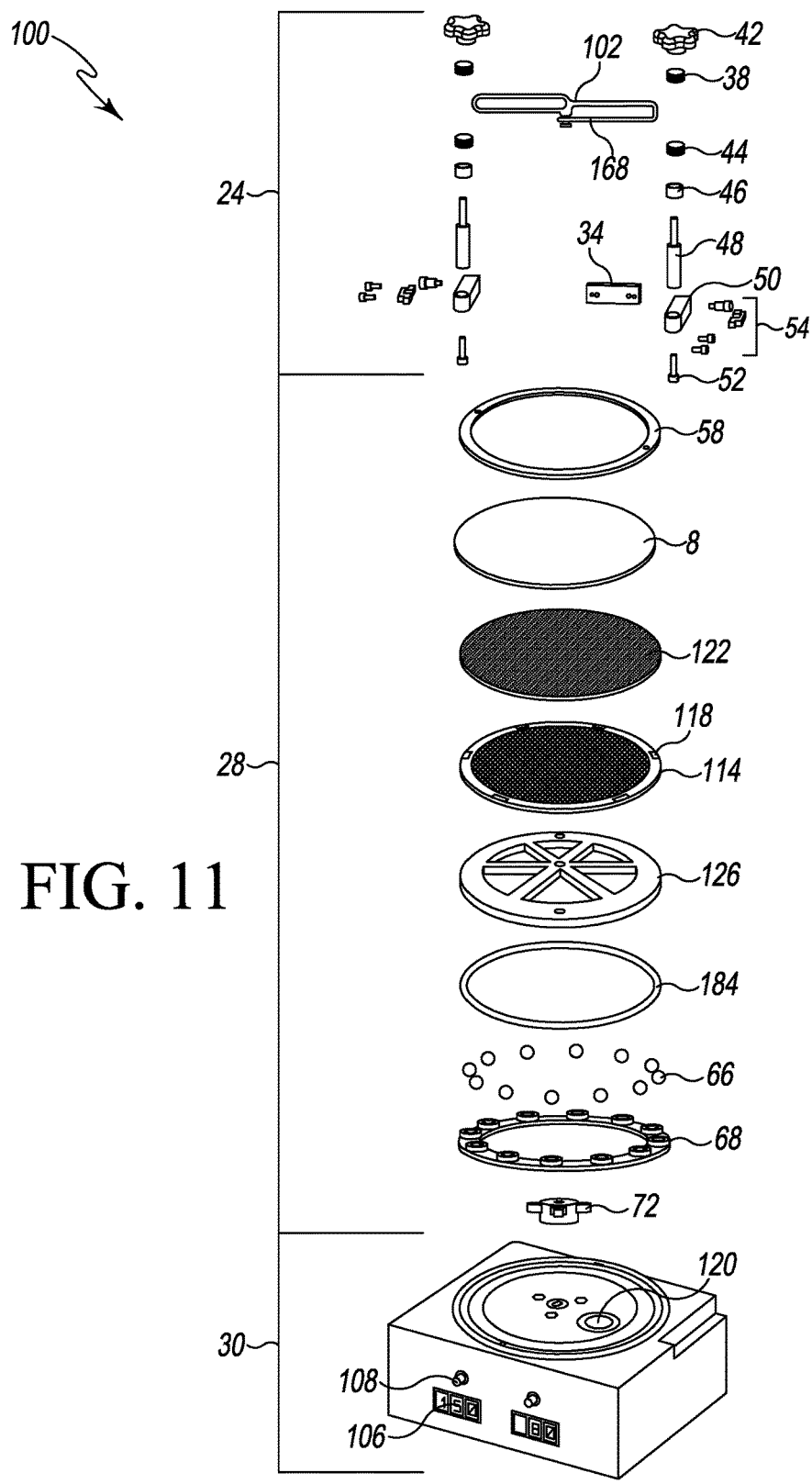
FIG. 11 is an exploded view of the swiping device of FIG. 9A with a PVA membrane mold and a cushion layer inserted between steel ring and vacuum.

Various views of a vacuum device (100) are shown (see FIGS. 9-11). An embodiment of the vacuum device (100) with an eight-inch rotating plate (126) that secures a PVA mold (8) is shown in FIGS. 9A-9B. As shown in the perspective and the front views of the vacuum device (100) of FIGS. 9A and 9C, respectively, the device (100) is comprised of an upper or blade assembly (24), a middle vacuum platter assembly (28), and a lower base assembly (30). A top panel (98) defines the vacuum platter assembly (28) from the lower base assembly (30) of the device (100).

Referring now to FIGS. 9A-9C, the lower base assembly (30) comprises a front panel (104) with which an operator interacts to control the device (100). In one embodiment, the front panel (104) may comprise one or more switches (180) and one or more knobs (108) to control the device (100) components. For example, as shown in FIG. 9C, the front panel (104) may comprise a left switch (180) that an operator may manually move up and down to turn on and off, respectively, the power of the spindle motor (76, see FIG. 10B). The right switch (180) of the front panel (104) may also be moved up and down by an operator to turn on and off, respectively, the power to the vacuum motor (112, see FIG. 10B). Additionally, an operator may turn a center knob (108) on the front panel (104) in order to control the rotating speed of the vacuum device (100).

Alternatively, another embodiment of a front panel (104) of a vacuum device (100) shown in FIGS. 9A and 10A may comprise one or more LED monitors (106) in addition to one or more knobs (108). For example, the left knob (108) may be turned on or off by an operator and further turned up or down to increase or decrease, respectively, the speed of the spindle motor (76) which controls the plate (18) rotation. The left LED monitor (106) corresponds to the left knob (108) and displays the speed of the rotating plate (18). The right knob (108) of the front panel (104) controls the vacuum power. Accordingly, the right knob (108) may be manually turned on by an operator and turned up or down to increase or decrease, respectively, the speed of the vacuum motor (112, see FIG. 10B). The right LED monitor (106) corresponds to the right knob (108) and displays the speed of the vacuum.

FIG. 9A shows a perspective view of the vacuum device (100) comprising the blade assembly (24) and the vacuum platter assembly (28). The blade assembly (24) comprises a single crossbar (102) which securely holds a swiping blade (34) on the right side between two knobs (42) which adjust the height of the blade (34). Drug-polymer solution is supplied to the blade (34) via one or more portals (128) and one or more reservoirs (130, see FIGS. 12-15) within the blade (34) and further distributed to the underlying PVA mold (8) atop the rotating plate (18).

FIG. 9D shows a side view of the vacuum device (100) comprising the upper blade assembly (24) and the vacuum platter assembly (28) atop the top panel (98) of the base assembly (30). FIG. 9E shows the back view of the vacuum device (100) with the vacuum platter assembly (28) atop the top panel (98) of the lower base assembly (30). Additionally, the back side of the base (30) comprises a vent (110). The vent (110) is designed to allow air, heat, or moisture produced from the vacuum motor (112) and spindle motor (76, see FIG. 10B) to escape from the base (30) which aids in securing the PVA membrane (8) to the vacuum disk (114, see FIG. 11).

Referring back to FIG. 9A which shows a perspective view of the device (100) comprising an upper assembly (24) and a vacuum platter assembly (28) atop a lower base assembly (30). In contrast, FIG. 10A shows a perspective view of the device (100) comprising a lower base assembly (30) without the upper blade assembly (24) or the vacuum platter assembly (28). FIG. 10B further depicts the inside of the base housing (30) comprising three main components: 1) a spindle motor (76) for rotating the vacuum disk (114), 2) a vacuum motor (112), and a circuit board (116) for digital display of the rotating speed and vacuum strength. A spindle motor (76) provides the rotation movement and speed, ad a vacuum motor (112) provides the vacuum supply.

FIG. 10C shows a plan view of the base assembly (30) of the vacuum device (100) with the base assembly (30) open, the vacuum platter assembly (28) absent, and the base (30) further comprising a vacuum line. A circular aperture (120) at the right bottom of the center plate (18) is connected to the vacuum motor (112). The vacuum motor (112) generates a vacuum that is delivered to the rotating vacuum platter (18)

via the vacuum line and the aperture (120) in order to keep the membrane (8) adhered to the plate (18) during swiping. The aperture (120) may be from about 3 cm to about 5 cm in diameter, and generally, is around 4 cm in diameter.

Referring now to FIG. 11, an exploded view of the vacuum device (100) is shown to include a blade assembly (24), a vacuum platter assembly (28), and a base assembly (30). The blade assembly (24) is comprised of a set of two knobs (42) that are turned manually to raise or lower a blade (34) held in a crossbar (102) for tight contact between the blade (34) and the PVA mold (8) on the vacuum platter assembly (28). Two sets of springs (38 and 44) absorb upward force from the blade (34) which is securely anchored inside the right chamber of the crossbar (102) with a latch (168) and one or more pins. Cylinders (46) provide a solid surface for the springs (38 and 44) to rest on and help adjust the height of the crossbar (102).

Components 38, 42, 44, 46, and 102 are anchored to the upper blade assembly (24) by a set of threaded dowels (48). The threaded dowels (48) are attached to arms (50) using screws (52), and the arms (50) are attached to a base (30) of a vacuum swiping device (100). The arms (50) allow the blade assembly (24) to be vertically rotated 180° for easy insertion and removal of the PVA mold (8) on the vacuum disk (114). An upper lock assembly (54) is attached to the sides of the arms (50) to secure the blade assembly (24) to the base (30). The blade assembly (24) is designed to secure the swiping blade (34) so that it maintains intimate contact with the underlying PVA mold (8).

The vacuum platter assembly (28) of the vacuum device (100) may have an eight-inch circular, rotating vacuum disk (114) in the center. The vacuum disk (114) secures a PVA mold (8) atop a cushion layer (122) and a magnetic steel ring (58) using vacuum suction while the disk (114) rotates. The circular vacuum disk (114) comprises a plurality of slots (118) to fit or accommodate magnetic bars (56, see FIG. 4) on its rim. The magnetic bars (56) on the vacuum disk (114) interact with the magnetic steel ring (58) to secure the PVA mold (8) and the cushion layer (122) between the ring (58) and the disk (114) during swiping.

The cushion layer (122, see FIG. 11) provides flexibility to the PVA mold (8) so that the membrane (8) remains flat and smooth for optimal delivery of a solution to the micro-cavities (6) of the membrane (8) during swiping by the blade (34). The cushion layer (122) may be made from any material that is flexible, durable, and does not prevent air flow in order to maintain vacuum. For example, the cushion layer (122) may be made of a porous plastic sheet or a porous cellulose membrane. The vacuum that holds the PVA mold (8) and the cushion layer (122) on the vacuum disk (114) is maintained by preventing leakage of the vacuum using an O-ring (184) placed outside of a supporting plate (126) which supports the vacuum disk (114).

The circular vacuum disk (114) may be made of any material that may be made to be porous so as to convey a vacuum. For example, the vacuum disk (114) may be comprised of a plastic or a metal, such as aluminum or stainless steel. Similarly, the supporting plate (126) may also be made of a plastic or a metal, such as aluminum or stainless steel. The circular vacuum disk (114) is made to rotate while the drug-polymer solution is introduced by a swiping blade (34) to the micro-cavities (6) in the PVA mold (8). The vacuum disk (114) is rotated freely with the help of a plurality of ball bearings (66).

Directly below the supporting plate (126) and the O-ring (184) in the vacuum platter assembly (28) are a plurality of ball bearings (66) and a ball bearing race ring (68) that may house or hold the ball bearings (66). The ball bearings (66) ensure smooth and level rotation of the plate (126) by reducing friction and bearing load from the upper assembly (24) onto the vacuum platter assembly (28) which sits atop the lower base assembly (30) as shown in detail in FIG. 11. Generally, the ball bearings (66) have a diameter ranging from about 8 mm to about 12 mm, and may be about 9.5 mm. The number of ball bearings (66) is not limited and may be from about three to about twenty and generally, is about twelve as shown in FIG. 11.

The vacuum assembly (28) is attached to the motor assembly of the base (30) via the rotating shaft (72) and the shaft base (80, see FIG. 10B). The shaft (72) and the shaft base (80) provide the movement for the rotation from the spindle motor (76) to the vacuum platter assembly (28) such that the disk (114) is rotated under the blade (34).

The swiping blade (34) contains a solution, for example, a drug-polymer solution, that is swiped over the PVA mold (8) and into the micro-cavities (6). The solution may be introduced directly to the blade (34) via one or more portals (128) in the blade (34) which may also comprise one or more reservoirs (130). The solution may also be introduced to the blade (34) by other methods, such as, attaching a solution holder on the blade (34) or connecting a rubber tube (160, FIGS. 17D-17H) to the blade (34).

Figure 12:
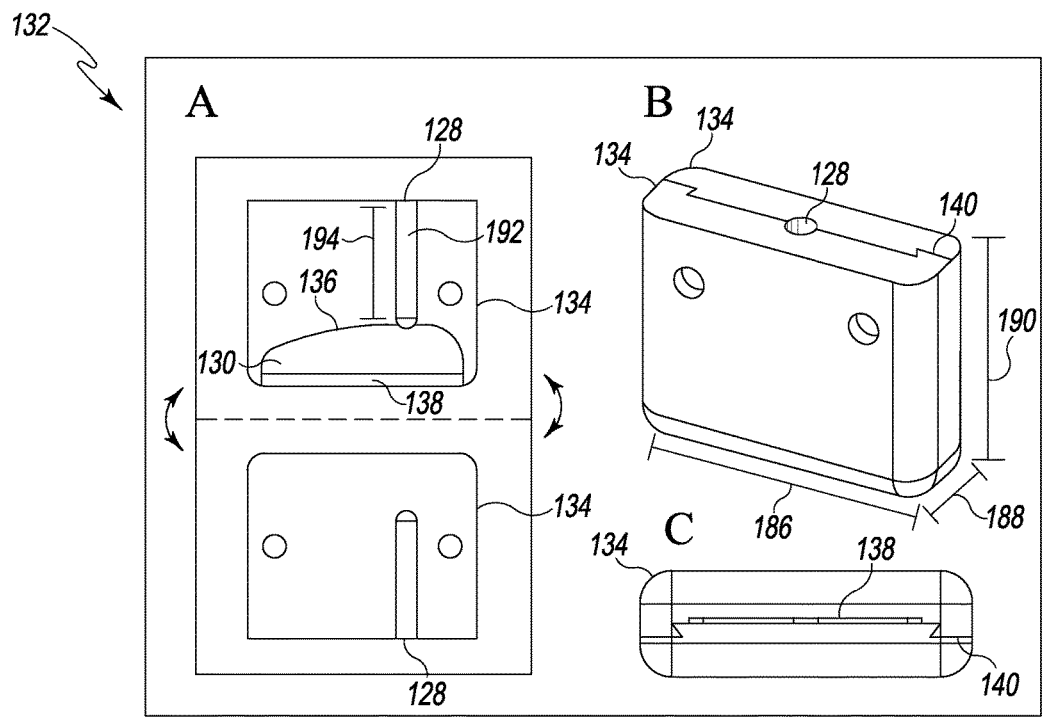
FIG. 12A is cross-sectional view of a four-inch blade component of the swiping device of FIG. 3A with a portal located on the right side.
FIG. 12B is a perspective view of a four-inch blade component of the swiping device of FIG. 3A with a portal located in the center.
FIG. 12C is a bottom view of the four-inch blade component of the swiping device of FIG. 12A.

A swiping blade (34) of the device (20) and the vacuum device (100) may have several embodiments. FIG. 12 shows a blade embodiment (132) for the four-inch device (20, see FIG. 3A), hereinafter referred to as a "four-inch blade." A four-inch device blade (132) is produced by longitudinally cutting a block of DELRIN polymer matrix using a computer-controlled cutting machine into two halves (134, see FIG. 12A). The two blade halves (134), which may be combined to make a closed blade (132, see FIG. 12B), may each have a width ranging from about 3 mm to about 5 mm, from about 3 mm to about 4 mm, and may be about 3.5 mm. While the size of a four-inch blade (132) is not limited and may be formed in any dimensions that accommodate the four-inch device (20), generally, the four-inch blade (132) may have the following dimensions: from about 3 cm to about 4 cm, and may be about 3.2 cm in length (186); from about 0.5 cm to about 1.5 cm, and may be about 1 cm in width (188); and from about 2 cm to about 3 cm, and may be about 2.6 cm in height (190). The drug-polymer solution is introduced to the closed blade (132) manually or via an external syringe pump (166, see FIG. 17) and distributed from the closed blade (132) through one or more portals (128) as shown in FIGS. 12A-12B.

A drug-polymer portal (128) may be located in various locations in a blade (34). In the illustrative four-inch blade embodiments (132) of FIGS. 12A and 12C, a drug-polymer portal (128) is located on the right side near the right end of the blade (132). This right-side design of the four-inch blade (132) ensures that the portal (128) and reservoir (130) is located at the outer end of the round PVA membrane (8) for proper drug-polymer delivery through the dispensing canal (138) to micro-cavities (6). As shown in FIG. 12, a portal (128) of the four-inch blade (132) may extend from the top of the blade (132) to the top of a channel (136). While the size of a portal (128) is not limited and may be formed in any dimensions that accommodate the four-inch device (20), generally, a portal (128) of the four-inch blade (132) has a diameter of approximately 2 mm to about 5 mm and may be about 3 mm in diameter (192) with a length (194) ranging from about 1 cm to about 2 cm, and may be about 1.7 cm.

The four-inch blade (132) may also comprise a reservoir (130), one or more channels (136), and one or more canals (138) at the bottom of the blade (132) through which the drug-polymer solution is dispensed from the reservoir (130) onto the membrane (8, see FIGS. 12A and 12C). The channels (136) help ensure the free flow of solution from the portal (128) through the blade (132) into the reservoir (130) and the canal (138) and onto the PVA membrane (8). The channels (136) of the four-inch blade (132) may range in length from about 2 mm to about 10 mm.

In addition, as shown in FIG. 12B, a dovetail design (140) may be incorporated into the four-inch blade (132) to prevent leaking of the drug-polymer solution. The bottom view of the four-inch blade (132) in FIG. 12C, shows both the dovetail design (140) and the canal (138) are used to optimize the drug-polymer delivery to membranes (8). As compared to the four-inch blade design (132), delivery of drug-polymer solution via a blade (142, see FIG. 13) for the eight-inch device (20) requires migration of the drug-polymer solution to a much further distance on the membrane (8).

A cross-sectional view of several blade embodiments (142) for the eight-inch device, hereinafter referred to as "eight-inch blade(s)," are shown in FIGS. 13A-13D. The eight-inch blades (142) may be used on the swiping device (20) and the vacuum swiping device (100). Similar to the four-inch blade (132), the eight-inch blade (142) may be produced by cutting a block of polymer matrix (e.g., DELRIN) followed by detailed drilling, often performed using a computer-controlled 3D milling machine. The cutting machine renders the eight-inch blade (142) into two halves which are then combined to make a closed blade (142), similar to the four-inch blade (132) of the device (20) shown in FIG. 12A. The two blade halves of the eight-inch blade (142) may each have a width ranging from about 3 mm to about 5 mm, and may be about 3.5 mm. Alternatively, a whole piece of DELRIN may be drilled to produce a one-piece blade (142) of which cross-sectional views of various eight-inch blade embodiments (142) are shown in FIG. 13. While the size of an eight-inch blade (142) is not limited and may be formed in any dimensions that accommodates the eight-inch devices (20 or 100), generally, the eight-inch blade (142) may have the following dimensions: from about 6 cm to about 8 cm, and may be about 7 cm in length (196); from about 0.8 cm to about 1.8 cm, and may be about 1.3 cm in width (198); and from about 1 cm to about 3 cm, and may be about 1.9 or about 2 cm in height (200).

To ensure accurate and homogeneous drug-polymer delivery to the membrane (8), both the four-inch blade (132) and the eight-inch blade (142) embodiments comprise at least one portal (128) at the top of the blade (34) and one or more channels (136). The location of the portal (128) on the blade (132 or 142) should be considered, since the area of the PVA mold (8) nearer its perimeter is larger than the area of the mold (8) in its center. Thus, the drug-polymer portal (128) may be located in various locations on the blade (132 or 142) to optimize efficient delivery of the drug-polymer solution to the membrane (8).

Figure 13:
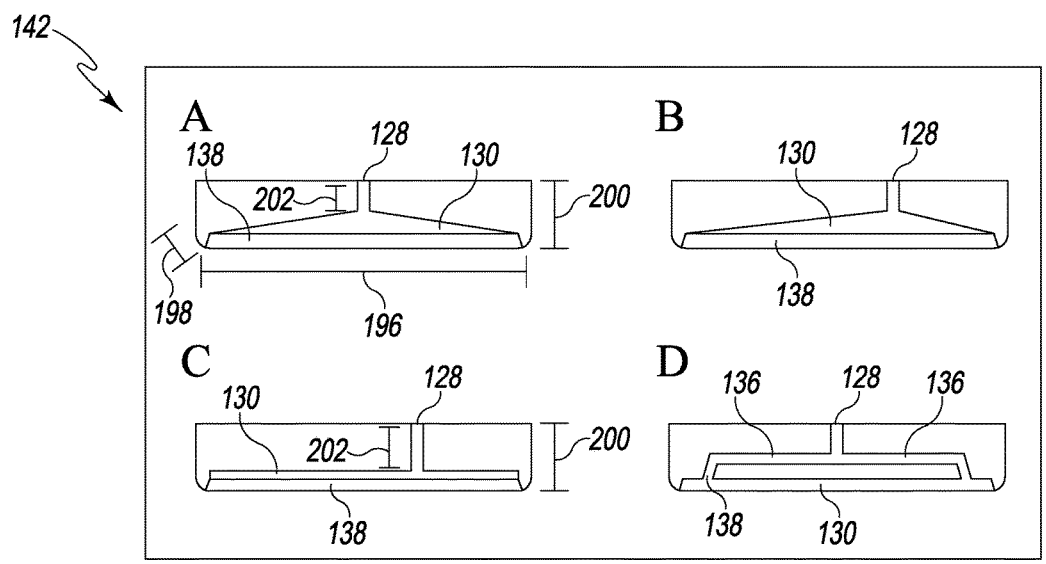
FIG. 13A is a cross-sectional view of an eight-inch blade component of the swiping device of FIG. 3B or 9A with a single-channel center portal and a triangular reservoir.
FIG. 13B is a cross-sectional of an eight-inch blade component of the swiping device of FIG. 3B or 9A with a single-channel portal located on the right side with a triangular reservoir.
FIG. 13C is a cross-sectional of an eight-inch blade component of the swiping device of FIG. 3B or 9A with a single-channel portal located on the right side with a rectangular reservoir.
FIG. 13D is a cross-sectional of an eight-inch blade component of the swiping device of FIG. 3B or 9A with a dual-channel center portal and a rectangular reservoir.

Referring now to FIG. 13, one or more portals (128) on the eight-inch blade (142) may be located in the center (see FIGS. 13A and 13D) or on the right side (see FIGS. 13B and 13C). While the size of a portal (128) is not limited and may be formed in any dimensions that accommodate the eight-inch vacuum device (100), generally, a portal (128) may have a diameter ranging from about 3 mm to about 5 mm, and may be approximately 4 mm in diameter. Additionally, a portal (128) may have a length (202) that extends from the top of the blade (142) to the top of the reservoir (130) and ranges from about 0.7 cm to about 1.7 cm, from about 1 cm to about 1.5 cm, and may be about 1 cm.

In an additional embodiment of the eight-inch blade (142), the portal (128) is divided into two separate channels (136, see FIG. 13D) to ensure uniform distribution and delivery of the drug-polymer solution from the blade (142) to the reservoir (130) to the PVA membrane (8) atop the eight-inch rotating plate (18 or 114) of the swiping device (20 or 100, respectively). While the size of a channel (136) is not limited and may be formed in any dimensions that accommodate the eight-inch vacuum device (100), generally, a channel (136) has a diameter of approximately 1 mm to about 2 mm and a length that ranges from about 3 cm to about 6 cm, and may be about 5.5 cm, as shown in FIG. 13D.

Since organic solvents are distributed through a cleaning blade and a swiping blade (34) of the aforementioned swiping devices (20 or 100), chemical-resistant materials may be used to form a blade (132 or 142). The use of chemical-resistant materials to form a blade (132 or 142) ensures that the blade (132 or 142) is resistant to chemicals and does not dissolve when exposed to the solvent of the drug-polymer solution during the dispensing process.

Examples of chemically resistant materials that may be used to form a blade or any blade embodiment (132 or 142) as described herein, are listed in Table 1 as polytetrafluoroethylene (PTFE), polyether Ether Ketone (PEEK), polyoxymethylene (POM), polyvinylidene Fluoride (PVDF), polypropylene (High-Clarity PP; (HCPP)), Teflon FEPv (Fluorinated Ethylene Propylene, FEP), Tefzel ETFE (ethylene tetrafluoroethylene; ETFE), Halar ECTFE (ethylene chlorotrifluoroethylene copolymer; ECTFE), Teflon TFE (tetrafluroethylene; TFE), and Teflon PFA (polyfluoroalkoxy; PFA). In particular, blades made of POM (e.g., DELRIN or acetal resin) and HCPP have been used with various solvents without any problems or signs of dissolution or degradation. Many of these blades were exposed to solvents, such as DCM, n-butyl acetate, dioxane, ethyl acetate (EA), benzyl alcohol (BA), and other different solvents or mixtures of solvents, for more than 100 hours with no observation of dissolution or degradation of the starting material.

TABLE 1

Polymeric materials used for making blades of the swiping device

| Abbreviation of Material | Full Name of Material |
| --- | --- |
| PTFE | Polytetrafluoroethylene |
| PEEK | Polyether Ether Ketone |
| POM (e.g., DELRIN) | Polyoxymethylene |
| PVDF | Polyvinylidene Fluoride |
| PP (HCPP) | Polypropylene (High-Clarity PP) |
| HDPE | High-Density Polyethylene |
| FEP | Teflon FEPv (Fluorinated Ethylene Propylene) |
| ETFE | Tefzel ETFE (Ethylene Tetrafluoroethylene) |
| ECTFE | Halar ECTFE (Ethylene Chlorotrifluoroethylene Copolymer) |
| TFE | Teflon TFE (Tetrafluroethylene) |
| PFA | Teflon PFA (Polyfluoroalkoxy) |

A scum layer is formed by escape of drug-polymer solution from a blade (34), for example, a four-inch blade (132) and an eight-inch blade (142), onto the PVA membrane (8). Even with the dovetail design (140) incorporated therein (see FIG. 12B or 12C), a four-inch blade (132) or an eight-inch blade (142) may allow escape of minimal amounts of drug-polymer solution onto the membrane (8). Solvent of the drug-polymer solution leaked from the blade (132 or 142) will evaporate fast resulting in a solid scum layer on the surface of the PVA mold (8) or the hydrogel mold (8). The scum layer formation results in unwanted loss of microparticles (10) and drug-polymer solution, particularly during large-scale production.

Figure 14:
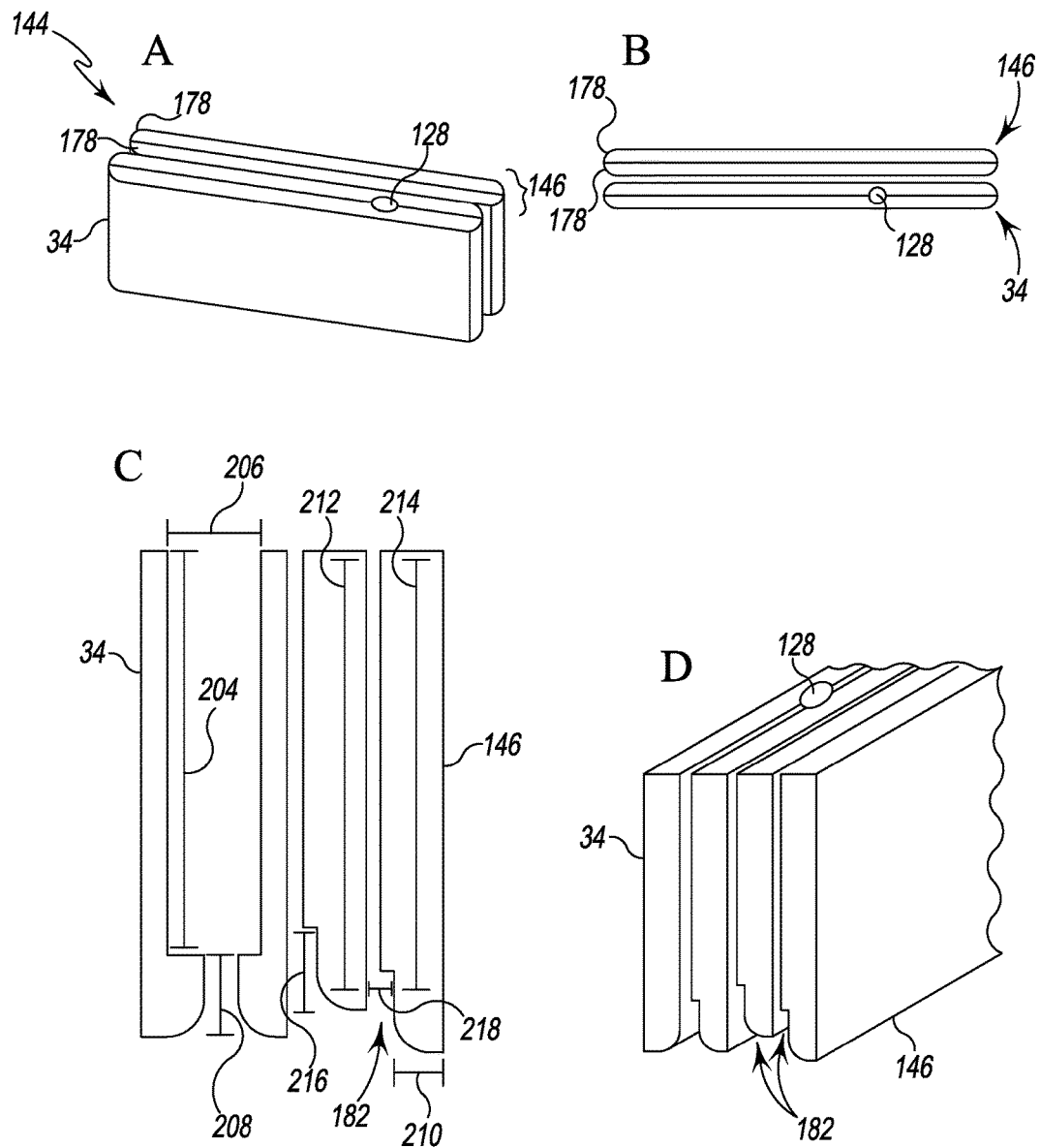
FIG. 14A is a perspective view of a dual-blade component of the swiping device of FIGS. 3C and 9A.
FIG. 14B is a plan view of the dual-blade component of FIG. 14A.
FIG. 14C is cross-sectional view of the dual-blade component of FIG. 14A.
FIG. 14D is a side elevation view of the dual-blade component of FIG. 14A.

To address a concern of scum layer formation in large-scale microparticle production using the swiping devices (20 and 100) of the present disclosure, an additional dual-blade embodiment (144) was designed (see FIG. 14). The dual-blade embodiment (144) is made of a main, blade (34), which may be a four-inch blade (132) or an eight-inch blade (142, 152, or 162), and a second blade (146) which is located right behind the main blade (34). The dual-blade (144) allows smooth flow of the drug-polymer solution through a portal (128) and channel (136) of the main blade (34) into the narrow micro-cavity space (6) of a PVA membrane (8) as described herein. For example, the drug-polymer solution may freely flow inside the main blade (34) to allow homogeneous distribution by the second blade (146) in contact with the PVA membrane (8).

A cross-sectional view of an eight-inch dual-blade embodiment (144) is shown in FIG. 14C. The main blade (34) of the dual-blade (144) comprises one or more portals (128) and one or more channels (136) to allow flow of the drug-polymer solution to the membrane (8). The portal (128) of the main blade (34) may have a length (204) ranging from about 1 cm to about 1.7 cm, and may be about 1.5 cm. A portal (128) of the main blade (34) may have a diameter (206) ranging from about 3 mm to about 5 mm, and may be about 4 mm. A channel (136) of the main blade (34) may have a length (208) ranging from about 2 mm to about 9 mm, and may be about 4 mm.

The second blade (146) of the dual-blade (144) may also be comprised of two halves (178) as shown in FIG. 14. The width (210) of each of the dual-blade halves (178) are similar to that of the main blade (34) and may range from 3 mm to about 3.5 mm, and may be about 3.2 mm. However, the length (212) of the inner half (178) of the dual-blade (144) may range from about 1.5 cm to about 1.9 cm, and may be about 1.85 cm. The length (214) of the outer half (178) of the dual-blade (144) may range from about 1.5 cm to about 2 cm and may be about 1.95 cm.

The second blade (146) of the dual-blade (144) is designed to remove a scum layer. Each half (178) of the second blade (146) of the dual-blade (144) comprises a recession (182) or a space between the end of the blade half (178) and a surface, for example, a surface of a mold or membrane (8). The recession (182) may have a length (216) ranging from about 3 mm to about 8 mm, and may be about 4 mm, as shown in FIG. 14C. The width (218) of the recession may be from about 0.2 mm to about 0.9 mm, and may be about 0.5 mm (see FIG. 14C).

When the dual-blade (144) interacts with the surface of a membrane (8) to disperse a solution during swiping, solvent of the solution, which may result in scum layer formation on the membrane (8), may be simultaneously removed. The scum layer is collected in the recession (182) of the dual-blade (144) during swiping and may manually be removed or cleaned from the dual-blade (144) after swiping has discontinued and the dual-blade (144) is removed from the device (20 or 100).

Implementation of the dual-blade design (144) on a device (20) and a vacuum device (100) reduces the formation of a scum layer significantly and increases microparticle (10) formation as compared to when a single blade (132 or 142) is used. When using the dual-blade design (144), microparticle (10) yields exceeded about 70% to about 80% (see Table 2), such that greater than about 70% of the starting drug-polymer solution was recovered as microparticles (10). Scum layer formation was almost negligible when PLGA polymers were used to produce goserelin microparticle formulations (10) using the dual-blade design (144). Low molecular weight PLGA polymers also showed negligible scum layer formation even when a single, main blade (132 or 142) was used. For example, PLGA polymers having a molecular weight ranging from about 35,000 g/mol to about 250,000 g/mol showed minimal to no scum formation when a single blade (132, 142, 152, or 162) or a dual-blade (144) was used to fill the micro-cavities (6) of the PVA membrane (8). Additionally, from about 40,000 g/mol to about 200,000 g/mol, from about 60,000 g/mol to about 150,000 g/mol, from about 100,000 g/mol to about 200,000 g/mol, from about 80,000 g/mol to about 120,000 g/mol, and from about 100,000 g/mol to about 110,000 g/mol of PLGA polymer showed minimal scum formation.

FIG. 15A shows a perspective view of one blade embodiment (152) of the vacuum swiping device (100). While the size of a blade (152) is not limited and may be formed in any dimensions that accommodate the eight-inch vacuum device (100), generally, the blade (152) may have the following dimensions: from about 6 cm to about 8 cm, and may be about 7 cm in length (220); from about 0.8 cm to about 1.8 cm, and may be about 1.3 cm in width (222); and from about 1 cm to about 3 cm, and may be about 1.9 or about 2 cm in height (224).

As shown in FIGS. 15A and 15B, the blade (152) may comprise multiple portals (128), an air vent (150) at the top of the blade (152), and an open space at the bottom of the front blade (see arrow) corresponding to the air vent (150) at the top of the blade (152). The air vent (150) is the small, circular opening on the left of the blade (152). The air vent (150) is designed to ventilate the air so that the drug-polymer solution may be easily distributed through the blade (152) and fill the reservoir (130) at the bottom of the blade (152) without any back flow. While the size of an air vent (150) is not limited and may be formed in any dimensions that accommodate the eight-inch vacuum device (100), generally, the air vent (150) has a diameter (226) ranging from of about 0.5 mm to about 1.5 mm, and may be about 1 mm with a length (228) ranging from about 1 cm to about 1.7 cm, and may be about 1.3 cm as shown in FIG. 15C.

Figure 15:
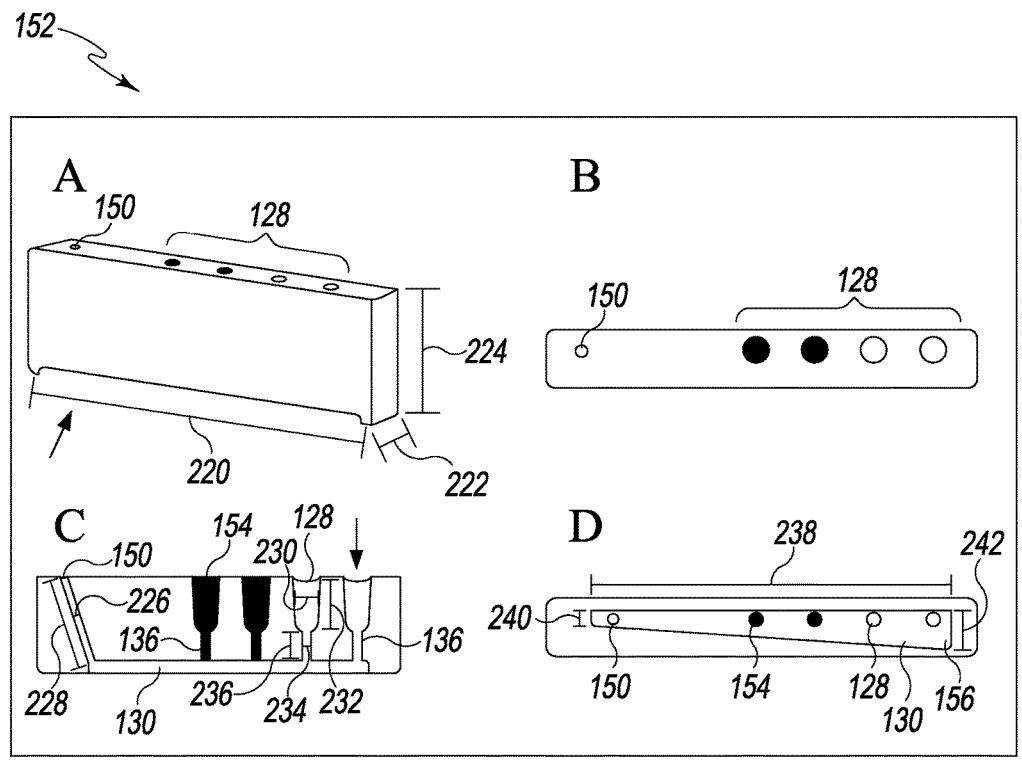
FIG. 15A is a perspective view of a first blade component of the swiping device of FIG. 9A with an open space corresponding to an air vent.
FIG. 15B is a plan view of the first blade component of the swiping device of FIG. 15A with an air vent and a plurality of portals.
FIG. 15C is a cross-sectional view of the first blade component of the swiping device of FIG. 15A with an air vent and a plurality of portals.
FIG. 15D is a bottom view of the first blade component of the swiping device of FIG. 15A with an air vent and a plurality of portals.
Figure 16:
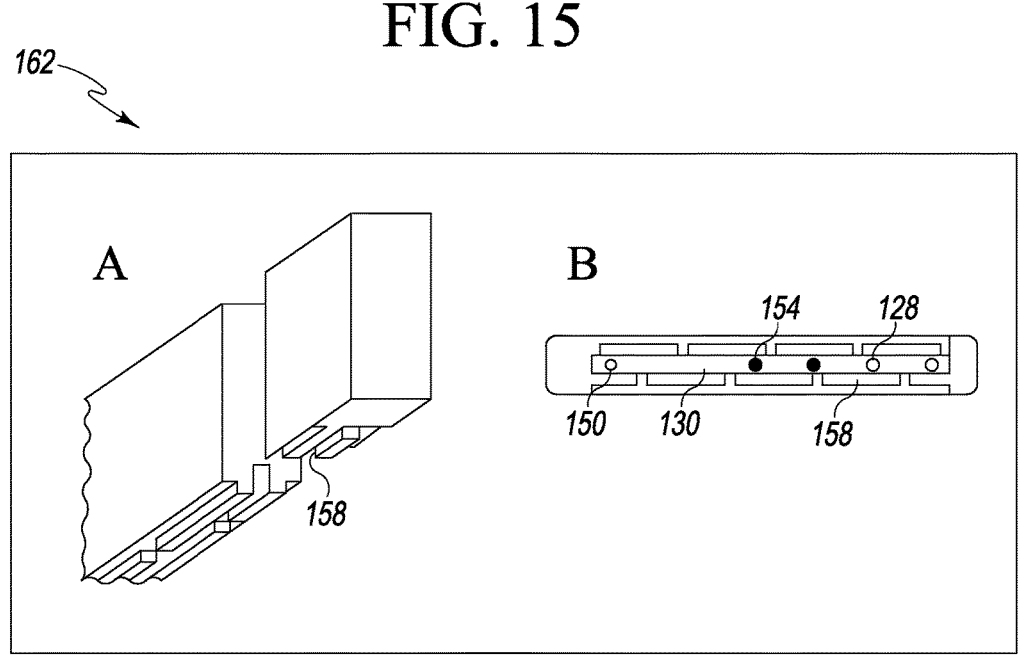
FIG. 16A is a fragmentary, cross-sectional view of a second blade component of the swiping device of FIG. 9A.
FIG. 16B is a bottom view of the second blade component of the swiping device of FIG. 16A with an air vent and a plurality of portals.

As shown in FIG. 15C, the portals (128) are connected to the reservoir (130) via channels (136) to enable delivery of the solution to the membrane (8). The portals (128) are responsible for introducing drug-polymer solution to the channels (136) which provide even distribution of the solution to the reservoir (130). The presence of multiple portals (128) and channels (136) as shown in FIGS. 15 and 16 allows easy and consistent spreading of drug/polymer solution on the mold or membrane (8).

Size and shape of portals (128) of the blade (152) are not limited and may be formed in any dimensions that accommodate the eight-inch vacuum device (100). In one embodiment (see FIG. 15C), the portals (128) are concave in shape and may have a diameter (230) of about 3 mm to about 6 mm, and may be about 5 mm with a length (232) ranging from about 5 mm to about 15 mm, and may be about 10 mm in length. Similarly, while the size of a channel (136) is not limited and may be formed in any dimensions that accommodate the eight-inch vacuum device (100), generally, the channel (136) has a diameter (234) ranging from about 0.5 mm and may be about 1.5 mm, and may be about 1 mm with a length (236) ranging from about 5 mm to about 15 mm, and may be about 7 mm as shown in FIG. 15C.

Only one of the portals (128), such as the first portal (see arrow in FIG. 15C), may be used for introducing the drug-polymer solution. Alternatively, a plurality of portals (128) on the blade (152) may be used to deliver the drug-polymer solution to the membrane (8). Unused portals (128) are closed using plugs (154, see FIG. 15C). Selection of the single position or multiple positions of a portal (128) to use in order to introduce the drug-polymer solution to a blade (152) depends on the properties of the solution, such as the solution viscosity and solvent type. Additionally, the location of the drug-polymer solution on the membrane (8) should be considered along with the number of microparticles (10) that are required to be produced.

Each portal (128) of the blade (152) may be disabled from distributing a solution to a blade reservoir (130) and onto the membrane (8) by inserting a plug (154). Plugs (154) may fill a portal (128) and a channel (136) and thus, may be formed into the portal (128) and channel (136) shape using a 3D milling machine or a 3D printing machine. Thus, plugs (154) have the same or similar dimensions as the portal(s) (128) and channel(s) (136) in which they fill.

Once formed, a plug (154) may be manually inserted into unneeded portals (128) and channels (136) such that the plug (154) fills the entire portal (128) and channel (136) so as to prevent solution flow through the plugged portal (128) and channel (136) as shown in FIG. 15C. Plugs (154) should not be introduced into the reservoir (130) so as to impede flow of the solution from the open portals (128) through the reservoir (130) and onto the membrane (8). Plugs may be prepared using any flexible materials that has the ability to be formed to tightly fit in the portal (128) so as to disable flow of a solution through the portal (128). For example, rubber is an elastic material from which plugs (154) may be formed. Additionally, polymers and materials that are used to make a blade (34, 132, 142, and 152) of the present disclosure (e.g., PEEK and PVDF) may also be used to form a plug (154).

FIG. 15C shows a cross-sectional view of the blade embodiment (152) for the vacuum device (100) comprising multiple portals (128) for introducing the dispensing solution to a reservoir (130), and an air ventilation hole (150). A blade (152) may have a plurality of portals (128) including from one portal to about ten portals, and generally has about four portals (128). The presence of an air vent (150) at the left of the blade (152) in FIG. 15C prevents formation of air bubbles which can lead to uneven distribution of the solution on the surface of the PVA mold (8) and result in a scum layer.

The bottom view of the blade (152) in FIG. 15D shows a reservoir (130) comprising an opening of the air vent (150) and the plurality of portals (128). The triangular shape (156) of the reservoir (130) on the bottom of the blade (152) provides more drug-polymer solution to the outer region of the PVA mold (8), since the surface area of the outer region of the mold (8) is much larger than the inner region of the mold (8) near the center. Additionally, the triangular shape (156) of the reservoir (130) enables the larger surface area of the PVA mold (8) to be supplied with a proper amount of the drug-polymer solution in order to efficiently prepare microparticles (10). The triangular shape (156) of the reservoir (130) also allows the open portals (128) of the blade (152) to collect any drug-polymer solution that may exist on the PVA mold (8) surface that may lead to formation of a scum layer. Rotation of the PVA membrane (8) on the swiping device (100) allows any solution that may form a scum layer to be redissolved in the solvent contained within the blade (152) such that no scum layer is formed.

While the triangular shape (156) of the reservoir (130) is not limited and may be formed in any dimensions that accommodate the blade (152), generally, the triangular shape (156) may have the following dimensions: from about 3 cm to about 6.5 cm, from about 4 cm to about 5.5 cm, from about 5 cm to about 5.5 cm in length (238), and may be about 5.2 cm in length; from about 3 mm to about 5 mm, and may be about 4 mm in height on one end (240); and from about 6 mm to about 10 mm, from about 7 mm to about 9 mm, and may be about 8 mm in height on the other end (242) as shown in FIG. 15D. The triangular shape (156) of the reservoir outlet (130) may be adjusted to other shapes, such as square, rectangular (see FIGS. 13C and 13D), circular, polygonal, trapezoidal, or other shapes, as necessary or desired.

FIG. 16A shows a cross-sectional, perspective view of another blade embodiment (162) for the vacuum device embodiment (100) designed to minimize a scum layer formation. The bottom view of the second blade (162) is shown in FIG. 16B. In comparison with the single reservoir (130) at the bottom of the first blade (152, see FIG. 15D), the second blade (162) has a greater number of open channels (158) at the bottom. When the blade (162) is swiped across a membrane (8), the open channels (158) remove scum layer formed on the PVA membrane (8) during the swiping process. While the second blade (162) is specifically designed to minimize or prevent scum layer formation on the membrane (8) during swiping, both the single reservoir embodiment of the first blade (152) and the open channel embodiment of the second blade (162) actively minimize or prevent scum layer formation during microparticle (10) production.

While all blades described herein may be used on the device (20) or vacuum device (100), the blade embodiments 152 and 162 (see FIGS. 15-16) present many advantages over blades 132, 142, and 144 (see FIGS. 13 and 14). For example, the vacuum device blades (152 and 162) have large inner reservoir space (130) to hold larger amounts of drug-polymer solution allowing more consistent production in size, shape, and drug-polymer content of microparticles (10). The reservoir (130) of the four-inch blade (132) may hold approximately 0.2 milliliters (mL) of drug-polymer solution, while the reservoir (130) of the eight-inch blades (142, 152, and 162) may hold a volume of solution ranging from about 0.5 mL to about 1.5 mL, from about 0.6 mL to about 1.2 mL, from about 0.6 mL to about 1.2 mL, and may be about 1 mL. Thus, the large reservoir space (130) held particularly inside blades (152 and 162) of FIGS. 15-16 enables easy dispensing of a drug-polymer solution to the PVA mold (8) without any external pressure (e.g., a syringe pump) as is required for other blades.

For example, an external force (e.g., a syringe pump) is required to effectively deliver the drug-polymer solution through the blade (132, 142, and 144) of the swiping device (20) and onto the membrane (8). A syringe pump (166) is not required to deliver the solution through the blade embodiments (152 and 162) of the vacuum device (100) because the blades (152 and 162) are designed to enable a gravity fed dispensing system of the solution to the membrane (8). However, a syringe pump (166) may be used with the vacuum device (100) blade embodiments (152 and 162) if necessary to deliver highly viscous drug-polymer solution to the membrane (8) via the blades (152 and 162).

Generally, low-viscosity polymers and high-viscosity drug-polymer solutions easily flow through the blades of the device (20) or vacuum device (100) to the PVA mold (8). The blade embodiments described herein (132, 142, 144, 152 and 162) are designed to effectively deliver a drug-polymer solution having a viscosity ranging from about 10 cPs (e.g., low-viscosity) to about 4,000 cPs, (e.g., high-viscosity). More specifically, the blade embodiments of the present disclosure will effectively deliver solutions ranging from about 50 cPs to about 3,500 cPs, from about 100 cPs to about 3,000 cPs, and from about 10 cPs to about 3,800 cPs, to a membrane.

Figure 17:
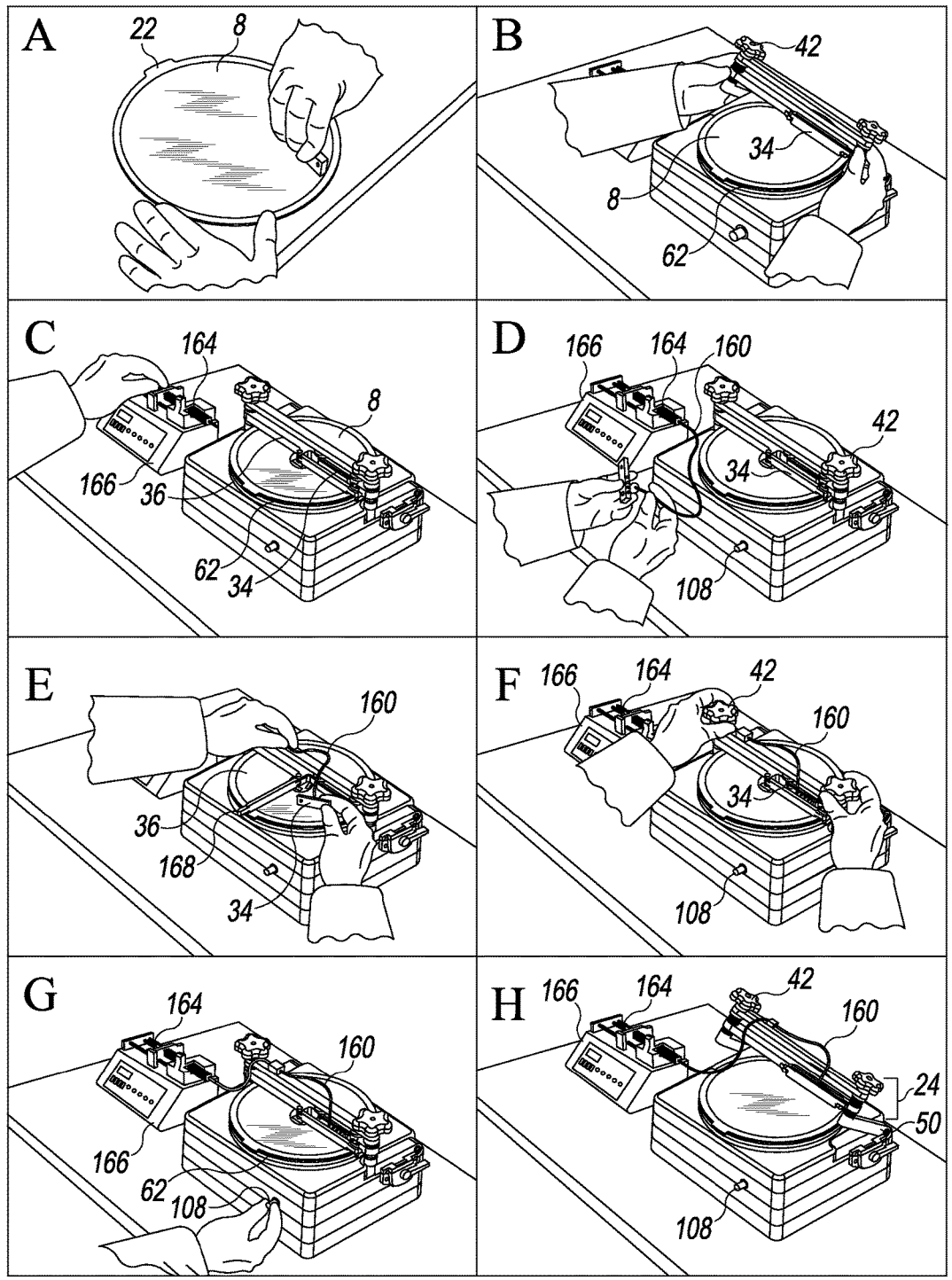
FIG. 17A shows a method step of placing a membrane on a rubber disk of the swiping device of FIG. 3B or 3C.
FIG. 17B shows a method step of securing the rubber disk to a metal plate and placing the plate on the swiping device of FIG. 3B or 3C.
FIG. 17C shows a method step of filling a syringe tube with a drug-polymer solution and placing the syringe tube on a syringe pump of the swiping device of FIG. 3B or 3C.
FIG. 17D shows a method step of connecting the syringe tube to a blade on the swiping device of FIG. 3B or 3C.
FIG. 17E shows a method step of placing the blade on a lower crossbar of the swiping device of FIG. 3B or 3C and closing a latch to secure the blade.
FIG. 17F shows a method step of lowering the blade to the mold by turning a knob atop of an arm on the swiping device of FIG. 3B or 3C.
FIG. 17G shows a method step of starting the syringe pump and rotating the plate and the membrane on the swiping device of FIG. 3B or 3C.
FIG. 17H shows a method step turning the knob to remove the filled membrane from the swiping device of FIG. 3B or 3C.

The method of using the swiping device (20) of the present disclosure to produce large-scale amounts of microparticles (10) will now be described. One method of using a swiping device (20) may include several steps as shown in FIG. 17. A PVA membrane (8) is placed on top of a rubber disk (22, see FIG. 17A). The rubber disk (22) is secured on a backing plate (18, see FIG. 17B). The backing plate (18) is placed on a rotating cover plate (62) or turn table of the device (20, see FIGS. 17B and 17C).

The drug-polymer solution may be introduced to the blade (34) from a syringe (164, see FIG. 17C) by various methods. For example, in one embodiment a rubber syringe tubing (160, see FIGS. 17D-17H) connects the solution to the blade (34). The free end of the rubber tubing (160) that is not attached to the blade (34) may be attached to the syringe (164) containing the solution. The syringe (164) may also be attached at its opposing end to a syringe pump (166) that is capable of dispensing the solution through the tubing (160) and into the blade (34, see FIGS. 17C and 17D). The blade (34) is placed on the lower crossbar (36) of the device (20), and a latch (168) or pins (174) are closed (see FIG. 17E).

The blade (34) is then lowered by rotating a knob (42) at the top of an arm (50, see FIG. 17F). As shown in FIG. 17G, the syringe pump (166) is started to introduce the drug-polymer solution to the blade (34) and swiping of the blade (34) is commenced by turning the knob (108) to initialize the spindle motor (76) and begin plate (62) rotation (i.e., via semi-automation). Once the micro-cavities (6) of the membrane (8) have been filled with solution, they may be refilled in order to completely pack the micro-cavities (6) with the solution. Refilling the micro-cavities (6) with solution comprises repeated rotation of the membrane (8) under the blade (34) to add more solution. The process of refilling the solution into the micro-cavities (6) may be repeated one or more times as necessary to achieve the desired properties of the resulting microparticles (10).

At the completion of the drug-polymer distribution and refilling process onto the membrane (8), the upper assembly (24) is raised to remove the filled membrane (8) of microparticles (10, see FIG. 17H). The membrane (8) may be air dried at a temperature ranging from about 20° C. to about 80° C., from about 25° C. to about 75° C., from about 40° C. to about 60° C., from about 30° C. to about 70° C., and from about 20° C. to about 60° C. such that the solvent of the solution may evaporate and the microparticles (10) may harden. Release of microparticles (10) from the membrane (8) occurs by dissolving the membrane (8) containing the microparticles (10) in water or a mixture of water and a solvent. The microparticles (10) are then ready for subsequent use.

Figure 18:
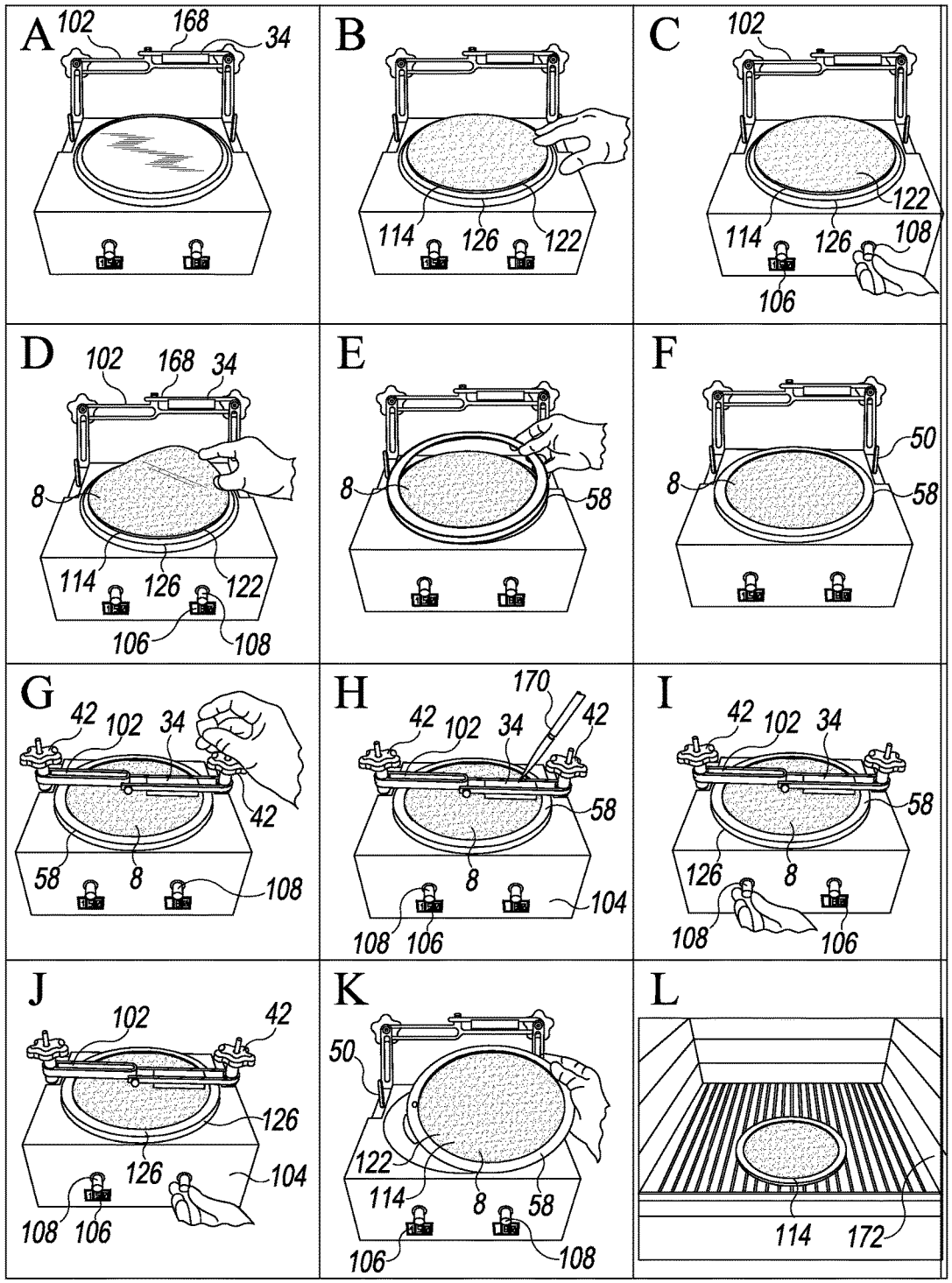
FIG. 18A shows a method step of by lifting a blade assembly of the swiping device of FIG. 9A.
FIG. 18B shows a method step of placing a cushion layer on a vacuum disk of the swiping device of FIG. 9A.
FIG. 18C shows a method step of turning on a vacuum switch of the swiping device of FIG. 9A.
FIG. 18D shows a method step of placing a PVA membrane mold on the swiping device of FIG. 9A.
FIG. 18E shows a method step of placing a steel ring on the swiping device of FIG. 9A.
FIG. 18F shows a method step of securing the PVA membrane with the steel ring on the swiping device of FIG. 9A.
FIG. 18G shows a method step of lowering the blade assembly to make intimate contact between a blade and the PVA mold of the swiping device of FIG. 9A.
FIG. 18H shows a method step of filling a reservoir in the blade with a drug-polymer solution of the swiping device of FIG. 9A.
FIG. 18I shows a method step of turning on a motor to rotate a vacuum platter of the swiping device of FIG. 9A.
FIG. 18J shows a method step of adjusting the speed of rotation of the vacuum platter of the swiping device of FIG. 9A.
FIG. 18K shows a method step of removing the PVA mold from the vacuum platter of the swiping device of FIG. 9A.
FIG. 18L shows a method step of drying the PVA mold in an oven.

A method of using a vacuum device (100) may include several steps as shown in FIG. 18. First, the blade (34) is placed on the crossbar (102) of the device (100) and the latch (168) is closed (arrow in FIG. 18A). A paper cushion layer (122) is placed on top of a vacuum disk (114, see FIG. 18B). Vacuum is turned on to secure the cushion layer (122) to the rotating plate (126, see FIG. 18C), and the PVA mold (8) is placed on top of the cushion layer (122, see FIG. 18D). The steel ring (58) is placed on top of the PVA mold (8, see FIG. 18E) using magnetic force to ensure the PVA mold (8) is without wrinkles (see FIG. 18F). The blade (34) is lowered by rotating the knobs (42) at the top of a set of arms (50, see FIG. 18G).

The drug-polymer solution may be filled inside a blade (34, see FIG. 18H) using a pipette (170) or other means. Knobs (108) on the front of the device (100) causes blade (34) swiping to begin by rotating the plate (126, see FIG. 18I) atop which the membrane (8) lies. The speed at which the plate (126) is rotated and the membrane (8) is swiped is controlled using a dial or knob (108) on the front panel (104) of the device (100, see FIG. 18J). At the completion of the drug-polymer dispensing process, the vacuum disk (114), the cushion layer (122), the PVA membrane (8), and the steel ring (58) are removed from the vacuum device (100, see FIG. 18K). The vacuum platter (114) is transferred to an oven (172) to remove the solvent and to dry and harden the microparticles (10, see FIG. 18L). The membrane (8) may be dried at a temperature ranging from about 20° C. to about 80° C., from about 25° C. to about 75° C., from about 40° C. to about 60° C., from about 30° C. to about 70° C., and from about 20° C. to about 60° C. Release of microparticles (10) from the membrane (8) occurs by dissolving the membrane (8) containing the microparticles (10) in water or a mixture of water and a solvent. The microparticles (10) are then ready for subsequent use.

Efficient addition of a drug-polymer solution to a membrane (8) may enable large-scale or industrial-scale production of microparticles (10) using the devices (20 and 100) described herein. One advantage of the semi-automated device (20) and vacuum device (100) described herein is that they facilitate a large-scale microparticle fabrication process.

EXAMPLES

As shown in Table 2, three criteria were measured to assess the swiping devices of the present disclosure (20 and 100) for large-scale microparticle production: 1) batch scale, 2) yield, and 3) currently good manufacturing practices (cGMP) as established by the U.S. Food and Drug Administration (U.S. FDA).

Example 1

TABLE 2

| Properties of the SpinSwiper Device and Vacuum SpinSwiper Device | |
|---|---|
| Criterion | Parameter |
| Batch scale* | >15 g/day Microparticle production |
| Yield | >80% (based on initial amount of drug-polymer mixture) |
| US FDA | Acceptable for cGMP production |

*Minimum amount of microparticles produced with a single device.

In one embodiment of the eight-inch device (20) and vacuum device (100), a PVA membrane (8) with cross-shaped designs resulted in about 300 mg of microparticle (10) production. Such yields require 50 PVA molds (8) to produce about 15 g of microparticles (10) per day for a single eight-inch swiping device (20 or 100). The amount of microparticle (10) yield increases as multiple devices (20 or 100) are used for microparticle (10) production. Further, in experiments using PLGA polymers to prepare a goserelin microparticle (10) formulation, the microparticle (10) yields were greater than about 80%.

It should be appreciated that the devices and methods described herein have broad utilities and applications. The device (20) and vacuum device (100) of the present disclosure meet the U.S.F.D.A. standards for cGMP production since the apparatuses are small, easily handled, and are sterilizable. For example, the device (20) and the vacuum device (100) and the methods of using the same may be used for microparticle (10) production in research laboratory, hospital, or clinical settings.

The foregoing embodiments were chosen and described in order to illustrate principles of the methods and apparatuses as well as some practical application. The preceding description enables others skilled in the art to utilize methods and apparatuses in various embodiments and with various modifications as are suited to the particular use contemplated. In accordance with the provisions of the patent statutes, the principles, and modes of operation of this device have been explained and illustrated in exemplary embodiments.

It is intended that the scope of the present methods and apparatuses be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

Use of the singular articles such as "a," "the," "said," etc. should be read to recite one or more of the indicated elements unless a claim recites an explicit limitation to the contrary. It is intended that the following claims define the scope of the disclosure and that the method and apparatus within the scope of these claims and their equivalents be covered thereby. In sum, it should be understood that the disclosure is capable of modification and variation and is limited only by the following claims.

What is claimed is:

1. A device for production of microparticles, comprising:
   an upper assembly comprising an upper top portion, an upper bottom portion, and a blade;
   a middle assembly comprising a middle top portion, a middle bottom portion, a plate, and a mold, wherein the mold is secured to the plate; and
   a lower assembly comprising a lower top portion, a lower bottom portion, and a motor,
   wherein the upper bottom portion of the upper assembly is secured to the middle top portion of the middle assembly and the middle bottom portion of the middle assembly is secured to the lower top portion of the lower assembly;
   wherein the plate is rotated directly under the blade by the motor, and
   wherein a solution is dispensed directly from the blade onto the mold.

2. The device of claim 1, wherein the lower assembly further comprises a vacuum motor.

3. The device of claim 1, wherein the upper assembly further comprises a set of arms to raise the upper assembly.

4. The device of claim 1, wherein the middle assembly further comprises a disk that is secured to the plate.

5. The device of claim 1, wherein the upper assembly further comprises at least one crossbar to secure the blade onto the upper assembly.

6. The device of claim 1, wherein the middle assembly further comprises a plurality of ball bearings, a ball bearing plate, and a ball bearing race ring that are secured to the motor to rotate the plate.

7. The device of claim 1, wherein the mold further comprises microcavities.

8. The device of claim 4, wherein magnets, a steel ring, an O-ring, or tape secure the disk to the plate.

9. The device of claim 4, wherein the disk comprises rubber, plastic, or metal.

10. The device of claim 7, wherein the mold comprises gelatin or PVA.

11. The device of claim 10, wherein the size of the mold ranges from about 9 cm to about 21 cm.

12. A blade of the device of claim 1, wherein the blade comprises one or more portals.

13. The blade of claim 12, wherein the one or more portals are located in the center of the blade or on the right side of the blade.

14. The blade of claim 12, wherein the one or more portals are connected to one or more reservoirs by one or more channels.

15. The blade of claim 12, wherein the one or more portals comprise a plug.

16. The blade of claim 12, wherein the blade further comprises a dovetail design.

17. The blade of claim 12, wherein the blade further comprises an air vent.

18. The blade of claim 14, wherein the reservoir may have a triangular shape.

19. A method of producing microparticles comprising:
   rotating the mold that is secured to the plate under the blade of the device of claim 7,
   dispensing the solution directly from the blade onto the microcavities of the mold,
   drying the mold, and
   releasing the microparticles.

20. A method of using the device of claim 19, wherein the method further comprises a vacuum to secure the mold to the plate.

* * * * *